US007820175B2

(12) United States Patent
Li et al.

(10) Patent No.: US 7,820,175 B2
(45) Date of Patent: Oct. 26, 2010

(54) HERBAL THERAPY FOR THE TREATMENT OF FOOD ALLERGY

(75) Inventors: Xiu-Min Li, Mamaroneck, NY (US); Hugh A. Sampson, Larchmont, NY (US)

(73) Assignee: Herbal Spring, LLC, Larchmont, NY (US)

( * ) Notice: Subject to any disclaimer, the term of this patent is extended or adjusted under 35 U.S.C. 154(b) by 0 days.

(21) Appl. No.: 10/592,914

(22) PCT Filed: Mar. 14, 2005

(86) PCT No.: PCT/US2005/008417

§ 371 (c)(1),
(2), (4) Date: Sep. 10, 2008

(87) PCT Pub. No.: WO2005/092360

PCT Pub. Date: Oct. 6, 2005

(65) Prior Publication Data

US 2008/0317878 A1    Dec. 25, 2008

Related U.S. Application Data

(60) Provisional application No. 60/554,775, filed on Mar. 19, 2004.

(51) Int. Cl.
*A61K 36/074* (2006.01)
(52) U.S. Cl. .................. 424/195.15; 424/728; 424/735; 424/739; 424/756; 424/773; 424/775; 424/777
(58) Field of Classification Search ........................ None
See application file for complete search history.

(56) References Cited

U.S. PATENT DOCUMENTS 6,630,176 B2    10/2003    Li et al.

FOREIGN PATENT DOCUMENTS

WO      WO 01/66122    *    9/2001
WO      WO 0166122          9/2001

OTHER PUBLICATIONS

Burks (Expert Opin. Pharmacother. (2008), vol. 9, No. 9, pp. 1145-1152).*
El-Shanawany (Clinical and Experimental Immunology (2008) vol. 153, pp. 1-9).*
International Search Report, PCT/US05/08417, date of mailing Jun. 9, 2005.
Written Opinion, PCT/US05/08417, date of mailing Jun. 9, 2005.
Li et al., "Novel approaches for the treatment of food allergy," *Current Opinion in Allergy and Clinical Immunology* 2:273-278 (2002).
Li et al., "Future Approaches to Therapy," In: Metcalfe DD, Sampson H A, Simon R A, eds. *Food Allergy: Adverse Reactions to Foods and Food Additives*, Baltimore: Blackwell Publishing (2004) pp. 561-569.
Loza et al., "Peanut allergy," *Clin Exp Allergy* 25:493-502 (1995).
Kattan et al., "Pharmacological and Immunological Effects of Individual Herbs in the Food Allergy Herbal Formula-2 (FAHF-2) on Peanut Allergy," *Phytother Res* 22:651-659 (2008).
Supplementary European Search Report for PCT/US2005008417, mailed Mar. 30, 2010.
Ko et al., "Effect of Chinese Herbal Formulas on T Cell Responses in Patients with Peanut Allergy or Asthma," *Journal of Allergy and Clinical Immunology* 138: S34 (2005).
Chen et al., "Study and Development of Food Allergy Herbal Formula (FAHF-2)," *Journal of Allergy and Clinical Immunology* 119: S113 (2007).
Wang et al., "Investigation of the Safety of the Food Allergy Herbal Formula (FAHF2) in Patients with Food Allergy—Phase 1," *Journal of Allergy and Clinical Immunology* 123: S176 (2009).
Srivastava, et al., "Silencing Peanut Allergy: A Chinese Herbal Formula, Fahf-2, Completely Blocks Peanut-induced Anaphylaxis for up to 6 Months Following Therapy in a Murine Model of Peanut Allergy," *Journal of Allergy and Clinical Immunology* 117: S328 (2006).
Srivastava, et al., "The Traditional Chinese Medicine Formula FAHF-2 Provides Complete Protection from Anaphylaxis in a Murine Model of Multiple Food Allergy," *Journal of Allergy and Clinical Immunology* 123: S151 (2009).
Kattan et al., "Pharmacological and Immunological Effects of Individual Herbs in the Food Allergy Herbal Formula-2 (FAHF-2) on Peanut Allergy," *Phytotherapy Research* 22: 651-659 (2008).
Srivastava et al., "A Chinese Herbal Medicine Formula, FAHF-2, Completely Blocks Anaphylaxis in a Murine Model of Peanut Allergy," *Journal of Allergy and Clinical Immunology* 113: S337 (2004).
Srivastava et al., "The Chinese herbal medicine formula FAHF-2 completely blocks anaphylactic reactions in a murine model of peanut allergy," *Journal of Allergy and Clinical Immunology* 115: 171-178 (2005).
Li et al., "Food Allergy Herbal Formula-1 (FAHF-1) blocks peanut-induced anaphylaxis in a murine model," *Journal of Allergy and Clinical Immunology* 108: 639-646 (2001).

* cited by examiner

*Primary Examiner*—Susan C Hoffman
(74) *Attorney, Agent, or Firm*—Brenda Herschbach Jarrell; Emilie Porter Huck; Choate, Hall & Stewart LLP

(57) ABSTRACT

The present invention provides herbal formulas, and compositions thereof, that can treat or reduce the severity, intensity, or duration of food allergy and food allergy related symptoms. The compositions may optionally include one or more adjuvants, cytokines, encapsulating materials, or pharmaceutically acceptable carriers or excipients, and may be administered prior to, during, or after the development of food allergy-related symptoms in a patient in need thereof.

10 Claims, 16 Drawing Sheets

Fig 1. Experimental protocol #1

Fig. 3 A. Anaphylactic symptom scores. Scores were determined 30 min following the last challenged. B. Plasma histamine levels. Plasma histamine levels were measured using of an enzyme immunoassay kit.[4] Symbols (open squares) indicate individual mice. Bars are means of 4-5 mice from each group.

HERBAL THERAPY FOR THE TREATMENT OF FOOD ALLERGY

CROSS REFERENCE TO RELATED APPLICATIONS

This Application claims the benefit under 35 U.S.C. §371 of International Application No.: PCT/US2005/008417, published as WO 2005/092360 A1, filed Mar. 14, 2005, which claims priority to U.S. provisional patent application 60/554,775, filed Mar. 19, 2004; the entire contents of each of which are hereby incorporated herein by reference.

FIELD OF THE INVENTION

The present invention relates generally to an herbal formulation. More particularly, the invention is directed to an herbal formulation consisting of a mixture of Chinese herbs useful for treating or lessening the severity of food allergy.

BACKGROUND OF THE INVENTION

Food allergy affects about 6-8% of children younger than four years of age, and about 2% of the United States population over ten years old, and the prevalence appears to be increasing. See Sampson H A. Food allergy. Part 1: Immunopathogenesis and Clinical Disorders. *J. Allergy Clin. Immunol.* 1999; 103:717-728. Food allergy is now the leading cause of anaphylactic reactions (approximately 31,000 cases annually) treated in hospital emergency departments in the United States. See Sampson H A. Clinical practice. Peanut allergy. *N Engl J Med* 2002; 346:1294-1299. It is known that only 8 foods account for 90 percent of the allergic reactions. They include peanuts, tree nuts (walnuts, pecans, etc.), fish, shellfish, eggs, milk, soy, and wheat. However, peanuts are the leading cause of severe allergic reactions, followed by shellfish, fish, tree nuts, and eggs.

Allergic reactions occur when an individual's immune system overreacts, or reacts inappropriately, to an encountered antigen. No allergic reaction is thought to occur the first time an individual is exposed to a particular antigen. However, the initial immune response to an antigen primes the system for subsequent allergic reactions. In particular, the antigen is taken up by antigen presenting cells (e.g., macrophages or dendritic cells) that degrade the antigen and then display antigen fragments to T cells. The activated T cells respond by secreting a collection of cytokines that affect other cells of the immune system. The profile of cytokines secreted by responding T cells determines whether subsequent exposures to the particular antigen will induce allergic reactions. When T cells respond by secreting interleukin-4 (IL-4), the effect is to stimulate the maturation of B cells that produce IgE antibodies specific for the antigen. These antigen-specific IgE antibodies then attach to specific receptors on the surface of mast cells and basophils, where they act as a trigger to initiate a rapid reaction to subsequent exposures to the antigen.

When the individual next encounters the antigen, it is quickly bound by these surface associated IgE molecules. Each antigen typically has more than one IgE binding site, so that the surface bound IgE molecules quickly become cross-linked to one another through their simultaneous (direct or indirect) associations with antigen. Such cross-linking induces mast cell degranulation, resulting in the release of histamines and other substances that induce the symptoms associated with allergic reaction. Individuals with high levels of IgE antibodies are known to be particularly prone to allergies.

Peanut allergy, which account for two thirds of cases of fatal anaphylactic shock, develops at an early age where the first reactions occur at a median age of 14 months. See Bock S A, Munoz-Furlong A, Sampson H A. Fatalities due to anaphylactic reactions to foods. *J. Allergy Clin. Immunol.* 2001; 107:191-193; and Sicherer S H, Furlong T J, Munoz-Furlong A, Burks A W, Sampson H A. A voluntary registry for peanut and tree nut allergy: characteristics of the first 5149 registrants. *J Allergy Clin Immunol* 2001; 108:128-132. Most anaphylactic reactions to peanuts (PN) occur in preschool and day care, and school exposure represents the first reaction for 25% of these children. See Sicherer S H, Furlong T J, DeSimone J, Sampson H A. The US Peanut and Tree Nut Allergy Registry: characteristics of reactions in schools and day care. *J Pediatr* 2001; 138:560-565. Because of these features of peanut allergy and because most PN allergic reactions are caused by inadvertent ingestion, peanut allergy has a severe negative effect on the quality of life of children and their families. See Primeau M N, Kagan R, Joseph L, Lim H, Dufresne C, Duffy C, Prhcal D, Clarke A. The psychological burden of peanut allergy as perceived by adults with peanut allergy and the parents of peanut-allergic children. *Clin Exp Allergy* 2000; 30:1135-1143.

Peanut allergy is an IgE mediated type I hypersensitivity in which allergen-specific IgE antibodies that bind to high affinity receptors (FcεRI) on the surface of mast cells and basophils. In patients with food allergy, re-exposure to the relevant foods triggers degranulation of mast cells/basophils resulting in the release of histamine and other mediators, which provoke symptoms of anaphylaxis. Early symptoms of food-induced anaphylaxis often include oral pruritus, colicky abdominal pain, nausea, vomiting, and diarrhea, cutaneous flushing, urticaria, and angioedema. Progressive respiratory symptoms, hypotension, and dysrhythmias typically develop in fatal and near fatal cases. See Yocum M W, Butterfield J H, Klein J S, Volcheck G W, Schroeder D R, Silverstein M D. Epidemiology of anaphylaxis in Olmsted County: A population-based study. *J. Allergy Clin. Immunol.* 1999; 104:452-456. Numerous studies have shown that Th2 cytokines are central to the pathogenesis of allergic disorders. See Romagnani S. The role of lymphocytes in allergic disease. *J. Allergy Clin. Immunol.* 2000; 105:399-408.

At the present time, there is no treatment for PN allergy. In the case of severe anaphylactic shock, epinephrine is often administered, either by self-injection (e.g. using the EpiPen®) or as an emergency treatment. Epinephrine rapidly constricts the blood vessels, relaxes the muscles in the airway and lungs, reverses swelling, and stimulates heartbeat, thereby reversing the most dangerous effects of an anaphylactic reaction. However, this treatment does not treat the allergic disorder itself. Furthermore, side effects of epinephrine may be severe and include palpitations, tachycardia (an abnormally fast heartbeat), sweating, nausea and vomiting, and respiratory difficulty and cardiac arrhythmias may follow administration of epinephrine.

Traditional immunotherapy is not an option for peanut allergy because of the high incidence of adverse reactions and low rate of maintenance of tolerance. See Nelson P A, Akselband Y, Dearborn S M, al-Sabbagh A, Tian Z J, Gonnella P A, Zamvil S S, Chen Y, Weiner H L. Effect of oral beta interferon on subsequent immune responsiveness. *Ann. N.Y. Acad. Sci.* 1996; 778:145-155; and Nelson H S, Lahr J, Rule R, Bock A, Leung D. Treatment of anaphylactic sensitivity to peanuts by immunotherapy with injections of aqueous peanut extract. *J. Allergy Clin. Immunol.* 1997; 99:744-751. The only way to manage peanut allergy is strict avoidance, but PN is a hidden ingredient in a number of processed foods and accidental ingestions are common. See Tariq S M, Stevens M, Matthews S, Ridout S, Twiselton R, Hide D W. Cohort study of peanut and tree nut sensitisation by age of 4 years. *BMJ* 1996; 313: 514-517; and Bock S A. The natural history of food sensitivity. *J Allergy Clin Immunol* 1982; 69:173-177. Furthermore, up to 55% of PN allergic children over a period of 5.4 years experience reactions following accidental ingestion. See Sicherer S H, Burks A W, Sampson H A. Clinical features of acute allergic reactions to peanut and tree nuts in children. *Pediatrics* 1998; 102:e6. This makes it urgent to develop approaches for peanut allergy.

Several new approaches to food allergy treatment are under. See Sampson H A. Immunological approaches to the treatment of food allergy. *Pediatr Allergy Immunol* 2001; 12:91-96; and Li X. M., Sampson H A. Novel approaches for the treatment of food allergy. *Current Opinion in Allergy and Clinical Immunology* 2002; 2:273-278. An ongoing clinical trial using monthly injections of humanized recombinant anti-IgE, appears to be somewhat effective in preventing allergic responses in PN-sensitive subjects to small amounts of PN protein. However, this treatment cannot cure the allergy, and continued protection would depend on monthly injections for an indefinite period of time.

One approach to treating allergies is antigen immunotherapy, which attempts to "vaccinate" a sensitive individual against a particular allergen by periodically injecting or treating the individual with a crude suspension of the raw allergen. The goal is to modulate the allergic response mounted in the individual through controlled administration of known amounts of antigen. If the therapy is successful, the individual's allergic response is diminished, or can even disappear. However, the therapy can require several rounds of vaccination, over an extended time period (3 to 5 years), and very often does not produce the desired results. Moreover, certain individuals suffer anaphylactic reactions to the vaccines, despite their intentional, controlled administration.

Another commonly used approach to treating allergic symptoms is the administration of histamine antagonists. These drugs are widely available in over-the-counter formulations, but unfortunately they merely mask the symptoms of the allergic response rather than providing any type of permanent cure or protection against recurrence.

Traditional Chinese Medicine (TCM) is one of the oldest medical practices in the world. The theoretical foundation of TCM described in Yellow Emperor's Inner Classic is believed to have been established in the first or second century C.E. TCM has been central in treating disease for centuries in Asia, and is still widely used in modern medical practice. Herbal medicines are increasingly being used by patients in Western countries to treat various diseases including allergy and asthma. See Association BM. Complementary Medicine: new approaches to good practice. Oxford: Oxford University Press, 1993; and De Smet P A. Herbal remedies. *N Engl J Med* 2002; 347:2046-2056. However a role for TCM in Western medicine is uncertain because of the lack of well-controlled studies confirming their reputed effects. Laboratory and clinical investigations regarding efficacy, safety and possible mechanisms of action are required.

SUMMARY OF THE INVENTION

The present invention encompasses the finding that a combination of herbs, or active components thereof, are useful for the treatment of food allergy. In particular, the present invention provides methods of treating or lessening the severity of food allergy, including but not limited to peanut allergy, in a patient in need thereof, comprising the step of administering to said patient an herbal formula of the present invention.

In certain embodiments of the present invention, said formula further comprises a pharmaceutically acceptable carrier, adjuvant, or vehicle.

In other embodiments of the present invention, said formula is administered in combination with one or more additional therapeutic agents. For example, the herbal formulas of the present invention may be administered in combination with anti-histamines, decongestants, cromolyn sodium, standard immunotherapy, rush immunotherapy, etc. used to treat allergic symptoms.

According to another aspect of the present invention, the herbal formula of the present invention may optionally be characterized in one or more animal model systems.

According to yet another embodiment, the present invention provides methods for identifying active components of the present herbal formula.

DEFINITIONS

As used herein, the following definitions shall apply unless otherwise indicated.

"Active component": An "active component" of an herb, herbal formulation, or preparation, is a compound or collection of compounds that is present in the herb, herbal formulation, or preparation and that, when separated from at least some other herbal components, retains at least some of a desired biological activity of the intact herb, herbal formulation, or preparation. In certain embodiments, the active component retains at least about 20% of the biological activity, or, alternatively, at least about 30%, 40%, 50%, 60%, 70%, 80%, 90%, 95%, or 99%.

"Allergen": An "allergen" is an antigen that (i) elicits an IgE response in an individual; (ii) elicits an allergic reaction (e.g., chronic airway inflammation characterized by eosinophilia, airway hyperresponsiveness, and excess mucus production), whether or not such a reaction includes a detectable IgE response; and/or (iii) elicits an allergic reaction (e.g., sneezing, watery eyes, puritis, diarrhea, anaphylaxis), whether or not such a reaction includes a detectable IgE response.

"Allergic individual": "Allergic individual" refers to an individual with sensitivities to particular antigens or allergens as exhibited by (i) eliciting an IgE response in an individual sufficient to cause a measurable clinical response; (ii) eliciting an allergic reaction (e.g., chronic airway inflammation characterized by eosinophilia, airway hyperresponsiveness, and excess mucus production), whether or not such a reaction includes a detectable IgE response; and/or (iii) eliciting the signs and symptoms of an allergic reaction (e.g., sneezing, watery eyes, puritis, redness, diarrhea, anaphylaxis), whether or not such a reaction includes a detectable IgE response. Such an individual has a reaction to a relatively innocuous antigen that does not cause a similar reaction upon exposure in most other members of the population. This reaction in an allergic individual can cause a harmful immune response and/or tissue damage. Symptoms of allergy may consist of exaggerated or pathological reaction (e.g., sneezing, respiratory distress, itching, or skin rashes) to substances, situations, or physical states that are without comparable effect on the average individual.

"Allergic reaction": An allergic reaction is a clinical response by an individual to an antigen. Symptoms of allergic reactions can affect the cutaneous (e.g., urticaria, angioedema, pruritus), respiratory (e.g., wheezing, coughing, laryngeal edema, rhinorrhea, watery/itching eyes), gastrointestinal (e.g., vomiting, abdominal pain, diarrhea), and/or cardiovascular (if a systemic reaction occurs) systems. In certain embodiments, the allergic reaction involves an IgE response in an individual sufficient to cause a measurable clinical response.

"Animal": The term animal, as used herein, refers to non-human animals, including, for example, mammals, birds, reptiles, amphibians, and fish. In certain embodiments, the non-human animal is a mammal (e.g., a rodent, a mouse, a rat, a rabbit, a monkey, a dog, a cat, or a pig). An animal may be a transgenic animal.

"Antigen": An "antigen" is (i) any compound or composition that elicits an immune response; and/or (ii) any compound that binds to a T cell receptor (e.g., when presented by an MHC molecule) or to an antibody produced by a B cell. Those of ordinary skill in the art will appreciate that an antigen may be a collection of different chemical compounds (e.g., a crude extract or preparation) or a single compound (e.g., a protein).

"Associated with": When two entities are "associated with" one another as described herein, they are linked by a direct or indirect covalent or non covalent interaction. In certain embodiments, the association is covalent. Desirable non covalent interactions include hydrogen bonding, van der Waals interactions, hydrophobic interactions, magnetic interactions, electrostatic interactions, etc. Also, two entities or agents may be "associated" with one another by being present together in the same composition.

"Cytokine": A "cytokine" is a small molecule that is released from or expressed by a cell and can alter the behavior or regulate the activity of one or more immunologically relevant target cells expressing a receptor for the cytokine. Cytokines that, if expressed by an antigen presenting cell, or by another cell, during presentation of antigen to a T cell would induce a particular response in that T cell can be classified according to the type of response they induce in the T cell. For example, cytokines that induce a Th1 response (e.g., IL-12, IL-2, IL-18, IL-10 or fragments thereof, IFNα, and/or IFNγ, etc.) are referred to herein as "Th1 stimulating cytokines"; cytokines that induce a Th2 response (e.g., IL-4, etc.) are referred to herein as "Th2 stimulating cytokines". Cytokines that are produced during a Th1 response (e.g., IFNγ, TNFβ, etc.) are referred to as "Th1 cytokines"; cytokines that are produced during a Th2 response (e.g., IL-4, IL-5, etc.) are referred to as "Th2 cytokines".

"Effective amount": The "effective amount" of an agent or composition refers to the amount necessary to elicit the desired biological response. The effective amount of the active components of an herb or herbal remedy is the amount necessary to decrease a particular sign and/or symptom (e.g., rhinorrhea, watery eyes, puritis, drop in blood pressure, drop in body temperature, level of IgE, production of cytokines, etc.) of an allergic reaction. The decrease may be a 10%, 20%, 30%, 40%, 50%, 60%, 70%, 80%, 90%, 95%, or 98% decrease. The effective amount of an active component of an herb or herbal remedy in a tolerizing composition is the amount that, when administered to an individual who is sensitized to an antigen, results in tolerization of the individual to the antigen.

"Herb": An "herb" according to the present invention includes any portion of the plant in which active components are found. For example, active components may be found one or more portions of a plant including in the leaves, flowers, stems, roots, seeds, spores, stalks, rhizomes, fruit, or fruiting bodies of said plant.

"Inducing agents": Inducing agents are compounds or other agents that induce a professional antigen presenting cell (pAPC) to produce stimulating cytokines. For example, if it is desired that a pAPC secrete Th1 stimulating cytokines, then factors such as LPS, CD40, CD40 ligand, BCGs, oligonucleotides containing CpG motifs, TNFα, and microbial extracts such as preparations of Staphylococcus aureus, heat killed Listeria, etc. can act as inducing agents ("Th1 inducing agents"). If instead it is desired that a pAPC secrete Th2 stimulating cytokines, then other factors (e.g., factors that induce IL-4 expression or inhibit IL-12 expression) can act as inducing agents ("Th2 inducing agents"). It will be appreciated by those of ordinary skill in the art that an inducing agent is usually an adjuvant.

"Isolated": As will be clear from context, the term "isolated" means (i) separated from at least one of the components with which the isolated entity or compound is associated in nature; and/or (ii) produced by a non-natural process (e.g., synthesized in vitro or produced by a recombinant organism).

"Mast cell": As will be apparent from context, the term "mast cell" is often used herein to refer to one or more of mast cells, basophils, and other cells with IgE receptors.

"Patient": According to the present invention, a "patient" means an animal, a mammal, and/or a human.

"Peptide": According to the present invention, a "peptide" comprises a string of at least three amino acids linked together by peptide bonds. The term "peptide" may refer to an individual peptide or a collection of peptides. For the purposes of the present invention, peptides may contain only natural amino acids. Alternatively, non natural amino acids (i.e., compounds that do not occur in nature but that can be incorporated into a polypeptide chain; see, for example, the web page at the following world wide web address: cco.caltech.edu/~dadgrp/Unnatstruct.gif, which displays structures of non-natural amino acids that have been successfully incorporated into functional ion channels) and/or amino acid analogs, as are known in the art, may be employed. Also, one or more of the amino acids in a "peptide" may be modified, for example, by the addition of a chemical entity such as a carbohydrate group, a phosphate group, a farnesyl group, an isofarnesyl group, a fatty acid group, a linker for conjugation, functionalization, or other modification, etc.

"Placebo": The term "placebo" (and related term "sham"), as used herein, refers to an inactive substance or preparation used as a control in an experiment or test to determine the effectiveness of an herbal formula of the present invention.

"Polynucleotide" or "oligonucleotide": The terms "polynucleotide" and "oligonucleotide" refer to polymers of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-amrinoadenosine, 2-thiothymidine, inosine, pyrrolo-pyrimidine, 3-methyladenosine, 5-methylcytidine, C5 bromouridine, C5 fluorouridine, C5 iodouridine, C5 propynyl uridine, C5 propynyl cytidine, C5 methylcytidine, 7 deazaadenosine, 7 deazaguanosine, 8 oxoadenosine, 8-oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, and hexose), and/or modified phosphate groups (e.g., phosphorothioates and 5' N phosphoramidite linkages).

"Purified": A compound is "purified" in accordance with the present invention if it is separated from substantially all other components. In certain embodiments, a purified compound is at least about 75% pure, or, alternatively, it is at least about 80%, 90%, 95%, 97%, 98%, or 99% pure.

"Sensitized individual": A "sensitized" individual is a human or animal who has been exposed to a given antigen and has mounted an immune response to that antigen that results in the display of one or more allergic symptoms when the individual is exposed to the antigen.

"Sensitized mast cell": A "sensitized" mast cell is a mast cell that has surface bound antigen-specific IgE molecules. The term is necessarily antigen specific. That is, at any given time, a particular mast cell will be "sensitized" to certain antigens (those that are recognized by the IgE on its surface) but will not be sensitized to other antigens.

"Sham": As used herein, the term "sham: is interchangeable with the term placebo. The term "sham" (and related term "placebo"), as used herein, refers to an inactive substance or preparation used as a control in an experiment or test to determine the effectiveness of an herbal formula of the present invention.

"Th1 response" and "Th2 response": Th1 and Th2 responses are well-established alternative immune system responses that are characterized by the production of different collections of cytokines and/or cofactors. For example, Th1 responses are generally associated with the production of cytokines such as IL-1β, IL-2, IL-12, IL-18, IFNα, IFNγ, TNFβ, etc.; Th2 responses are generally associated with the production of cytokines such as IL-4, IL-5, IL-10, etc. The extent of T cell subset suppression or stimulation may be determined by any available means including, for example, intra-cytoplasmic cytokine determination. In certain embodiments of the invention, Th2 suppression is assayed, for example, by quantitation of IL-4, IL-5, and/or IL-13 in stimulated T cell culture supernatant or assessment of T cell intra-cytoplasmic (e.g., by protein staining or analysis of MRNA) IL-4, IL-5, and/or IL-13; Th1 stimulation is assayed, for example, by quantization of IFNα, IFNγ, IL-2, IL-12, and/or IL-18 in activated T cell culture supernatant or assessment of intra-cytoplasmic levels of these cytokines.

DETAILED DESCRIPTION OF CERTAIN EMBODIMENTS OF THE INVENTION

Figure 1:
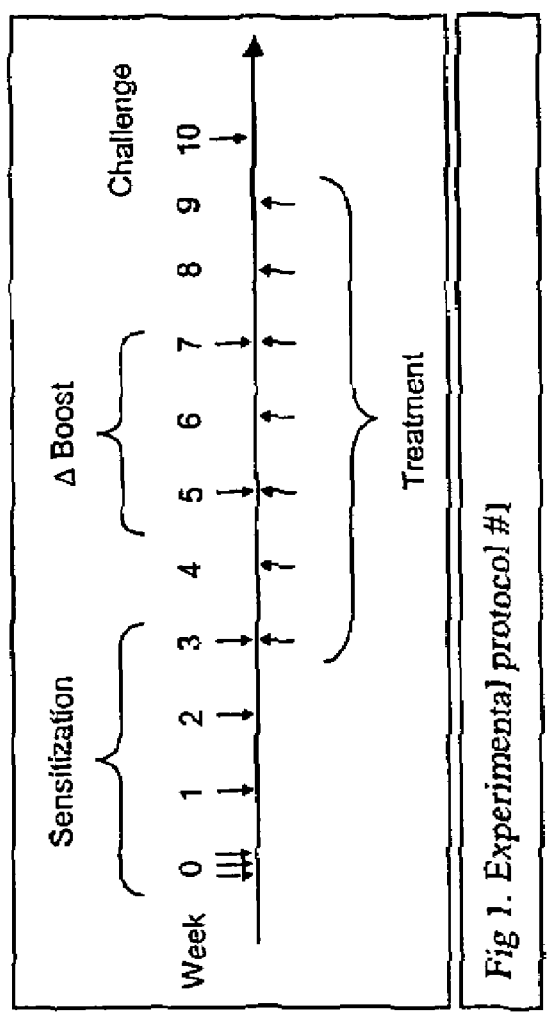
FIG. 1 depicts the dosing protocol #1.

The present invention unites insights from traditional Chinese medicine and modern Western medicine to formulate treatments for food allergy. Traditional Chinese medicine ("TCM") employs herbal formulations to treat bodily ailments. In some cases, single herbs or herb derivatives are used. More commonly, however, "formulas" or specific combinations of several particular herbs are administered. The recipes for these formulas are assembled into books known as "formularies". The original formulary, Discussion of Cold-Induced Disorders and Miscellaneous Diseases (Shang Han Za Bing Lun), was written at the end of the second century A.D. by Zhang Zhong-Jing. This book was later edited by Wang Shu-He, who divided it into two parts, Discussion of Cold-Induced Disorders (Shang Han Lun), which deals with externally-contracted diseases, and Essentials from the Golden Cabinet (Jin Gui Yao Lue), which is primarily concerned with internally-generated disorders (Bensky et al., Chinese Herbal Medicine: Formulas & Strategies. Eastland Press, 1999; incorporated herein by reference). These two books contain 374 formulas. The present invention provides a new herbal formula for the treatment of food allergy according to Western principles.

Unlike asthma and other allergic diseases, food allergy is not described in the TCM literature. Peanut allergy is very rare in China. However, there are TCM herbal formulas for treating gastrointestinal disorders such as vomiting, abdominal pain and diarrhea and "collapse" etc, the symptoms, of which are similar to food allergic reactions. In light of the gastrointestinal symptoms induced by food allergic reactions, and the Th2 dominant responses of food allergy, we developed an herbal formula designated FAHF-1 derived from a traditional Chinese herbal formula. We tested the efficacy of this formula in our murine model of peanut anaphylaxis that closely mimic human peanut allergy, and have been used over the past years to test various new approaches for treatment of peanut allergy. Li X. M., Sampson H A. Novel approaches for the treatment of food allergy. *Current Opinion in Allergy and Clinical Immunology* 2002; 2:273-278; Li X-M, Sampson H A. Future Approaches to Therapy. In: Metcalfe DD, Sampson H A, Simon R A, eds. Food Allergy: Adverse Reactions to Foods and Food Additives. Baltimore: Blackwell Publishing, 2004:561-569. We found that FAHF-1 markedly reduced mast cell degranulation and histamine release, and completely blocked PN-induced anaphylactic symptoms, reduced PN-specific serum IgE levels FAHF-1 also significantly reduced PN-induced lymphocyte proliferation, and IL-4, IL-5 and IL-13, but not INF-γ synthesis. No toxic effects on liver or kidney functions and no overall immune suppression were observed. Loza C, Brostoff J. Peanut allergy. *Clin Exp Allergy* 1995; 25:493-502.

However, FAHF-1 contained the two herbs Zhi Fu Zhi (Radix Lateralis Aconiti Carmichaeli Praeparata) and Xi Xin (Herba Asari). Considering various TCM formulation concepts, we concluded that these two herbs are may not be essential to the activity in this formula. Furthermore, in TCM practice, Zhi Fu Zi requires special processing and appropriate doses for Zhi Fu Zhi and Xi Xin are critical to ensure safety. Although the formula FAHF-1 itself has been shown to be safe, recent concern over residual aconitine in Zhi Fu Zhi and adulteration by aristolochic acid in Xi Xin has been expressed by FDA. Thus, elimination of these two herbs significantly reduces the effort required to ensure the quality and safety of the formula. To this end, we generated a modified formula, FAHF-2, which does not contain Zhi Fu Zhi and Xi Xin. One embodiment of the present invention relates to an herbal formulation useful for treating or lessening the severity of food allergy, in a patient in need thereof, said formulation comprising a mixture of herbs, or active components thereof, consisting of Ling-Zhi, Wu Mei, Chuan Jiao, Huang Lian (Chuan), Huang Bai (Chuan), Gan Jiang, Gui Zhi, Ren Shen (Hong), and Dang Gui (Shen).

Another embodiment of the present invention relates to an herbal formulation useful for treating or lessening the severity of one or more symptoms associated with food allergy, in a patient in need thereof, said formulation comprising a mixture of herbs, or active components thereof, consisting of Ling-Zhi, Wu Mei, Chuan Jiao, Huang Lian (Chuan), Huang Bai (Chuan), Gan Jiang, Gui Zhi, Ren Shen (Hong), and Dang Gui (Shen).

Yet another embodiment of the present invention relates to an herbal formulation useful for treating or lessening the severity of anaphylactic shock resulting from food allergy, in a patient in need thereof, said formulation comprising a mixture of herbs, or active components thereof, consisting of Ling-Zhi, Wu Mei, Chuan Jiao, Huang Lian (Chuan), Huang Bai (Chuan), Gan Jiang, Gui Zhi, Ren Shen (Hong), and Dang Gui (Shen).

The present invention provides an herbal formulation that reduces one or more allergic symptoms and signs including but not limited to tingling sensation in the mouth, swelling of the tongue and the throat, airway hyperresponsiveness, hives, rash, puritis, watery eyes, bronchoconstriction, edema, vomiting, abdominal cramps, diarrhea, difficulty breathing, vasodilation, decrease in blood pressure, increased IgE levels, increased plasma histamine levels, increased numbers of goblet cells, increased Th2 cytokine levels, bronchial inflammation, loss of consciousness, anaphylaxis, and death.

According to certain embodiments, the herbal formula of the present invention demonstrates a reduction in symptoms that is at least as significant as that observed with known therapeutic agents such as anti-histamines. According to other embodiments, the reduction in symptoms occurs more quickly than is seen with known therapeutic agents (e.g., conventional antigen immunotherapy and/or anti-histamine treatment), is more persistent than that observed with known therapeutic agents, and/or is more extensive than that achieved by known therapeutic agents.

Without wishing to be bound by any particular theory, we propose that inventive herbal compositions down regulate Th2 responses, thereby leading to a reduction in allergy symptoms. In fact, particularly preferred compositions have specific effects on Th2 responses, rather than general immunosuppressive activities. For example, the present compositions, when compared to immunosuppressive agents such as corticosteroids, FK506, methotrexate, and cyclosporine, are more selective for the allergic response.

The current understanding of allergic diseases may be used to choose herbal formulations that may be further tested using standard experimental systems used in studying allergies (for example, see Examples below). Formulations may be chosen which are known to reduce sneezing, water eyes, itching, diarrhea, wheezing, bronchoconstriction, hives, etc, as such symptoms can be associated with allergies. The chosen formulation may be assessed in animal models of allergy, or in in vitro models of allergy. From the hundreds of herbals formulas known in Eastern medicine, the present invention teaches methods of choosing potential anti-allergy therapies and testing the chosen therapies for efficacy in treating or preventing allergies. As described in the Examples below, the present invention also demonstrates use of these methods, and defines certain particularly useful compositions.

Herbs for use in the herbal formula of the present invention will generally be provided in their natural, herbal form. The herbs may be harvested from any location at any time of the year. According to certain embodiments, the herbal formulas have the active components at concentrations sufficient to treat food allergy symptoms. According to other embodiments, the herbs are harvested in a manner which maximizes the efficacy of the herbal composition.

The particular herbs selected for use in the formulas of the present invention may be chosen based on any number of criteria including, but not limited to, appearance (e.g., color, texture, etc.), smell, feel, HPLC "finger printing", chromatographic (e.g., HPLC, TLC, GC) fingerprint profiles, presence of a "marker" constituent, etc. In certain embodiments, the herbal composition is prepared by following the FDA's "Guidance for Industry Botanical Products", the entirety of which is incorporated herein by reference. The herbs may also be checked for the presence of pesticide residues, heavy metal content, etc. to ensure the safety of the final product.

As is appreciated by those skilled in this art, a variety of techniques are well known in the art for extracting, isolating, and/or purifying individual active components of the particular herbs. The present invention encompasses both the identification of such active components as described herein and the incorporation of such components into the formulas of the present invention as described herein.

Herbal Compositions

The nine herbs utilized in accordance with the present invention, Ling-Zhi, Wu Mei, Chuan Jiao, Huang Lian (Chuan), Huang Bai (Chuan), Gan Jiang, Gui Zhi, Ren Shen (Hong), and Dang Gui (Shen), are known and have been characterized individually. Their individual characteristics are summarized below in Table 1.

TABLE 1

Components of herbal medicines in FAHF-2

| | Name of TCM Materia Medica (Pin Yin) | Equivalent Pharmaceutical Name | Amount (g) | Part used |
|---|---|---|---|---|
| 1 | Ling Zhi (Chi) | Ganoderma Lucidum | 15-80 | Fruiting body |
| 2 | Wu Mei | Fructus Pruni Mume | 30-80 | Fruit |
| 3 | Chuan Jiao | Pericarpium Zanthoxyli Bungeani | 1.5-3 | Seed |
| 4 | Huang Lian (Chuan) | Rhizoma Coptidis | 9-15 | Root |
| 5 | Huang Bai | Cortex Phellodendri | 6-80 | Root |
| 6 | Gan Jiang | Rhizoma Zingiberis Officinalis | 6-15 | Root |
| 7 | Gui Zhi | Ramulus Cinnamomi Cassiae | 3-9 | Twig |
| 8 | Ren Shen (Hong) | Radix Ginseng | 9-15 | Root |
| 9 | Dang Gui (Shen) | Corpus Radix Angelicae Sinensis | 9-15 | Root |

Methods for preparing the individual herbs utilized in the present invention are known to one of ordinary skill in the art and include the teachings set forth in the Examples, below. In certain embodiments, the herbs prepared according to these teachings are combined to form the herbal formulas of the present invention.

In certain embodiments of the present invention, the herbal formula is prepared from about 15-80 grams of Ling-Zhi. Specifically, either about 15-80 grams of the herb Ling-Zhi itself is administered or an extract obtained from about 15-80 grams of Ling-Zhi is prepared and utilized as described hereinbelow.

In other embodiments of the present invention, the herbal formula is prepared from about 30-80 grams of Wu Mei. Specifically, either about 30-80 grams of the herb Wu Mei itself is administered or an extract obtained from about 30-80 grams of the herb Wu Mei is prepared and utilized as described hereinbelow.

In yet other embodiments of the present invention, the herbal formula is prepared from about 1.5-3 grams of Chuan Jiao. Specifically, either about 1.5-3 grams of the herb Chuan Jiao itself is administered or an extract resulting from about 1.5-3 grams of Chuan Jiao is prepared and utilized as described hereinbelow.

In other embodiments of the present invention, the herbal formula is prepared from about 9-15 grams of Huang Lian (Chuan). Specifically, either about 9-15 grams of the herb Huang Lian (Chuan) itself is administered or an extract obtained from about 9-15 grams of the herb Huang Lian (Chuan) is prepared and utilized as described hereinbelow.

In yet other embodiments of the present invention, the herbal formula is prepared from about 6-80 grams of Huang Bai. Specifically, either about 6-80 grams of the herb Huang Bai itself is administered or an extract resulting from about 6-80 grams of Huang Bai is prepared and utilized as described hereinbelow.

In other embodiments of the present invention, the herbal formula is prepared from about 6-15 grams of Gan Jiang. Specifically, either about 6-15 grams of the herb Gan Jiang itself is administered or an extract obtained from about 6-15 grams of the herb Gan Jiang is prepared and utilized as described hereinbelow.

In yet other embodiments of the present invention, the herbal formula is prepared from about 3-9 grams of Gui Zhi. Specifically, either about 3-9 grams of the herb Gui Zhi itself is administered or an extract resulting from about 3-9 grams of Gui Zhi is prepared and utilized as described hereinbelow.

In other embodiments of the present invention, the herbal formula is prepared from about 9-15 grams of Ren Shen (Hong). Specifically, either about 9-15 grams of the herb Ren Shen (Hong) itself is administered or an extract obtained from about 9-15 grams of the herb Ren Shen (Hong) is prepared and utilized as described hereinbelow.

In other embodiments of the present invention, the herbal formula is prepared from about 9-15 grams of Dang Gui (Shen). Specifically, either about 9-15 grams of the herb Dang Gui (Shen) itself is administered or an extract obtained from about 9-15 grams of the herb Dang Gui (Shen) is prepared and utilized as described hereinbelow.

In certain embodiments, it will be desirable to preserve the ratios of herbal components in the FAHF-2 formula.

The methods of isolating and characterizing each of the herbs of the present invention are known to one of skill in the art. Certain of these methods are set forth below.

Isolation of Active Components

Individual active components of the herbs or herbal formulations may be identified as described herein and may be isolated and/or purified using any techniques known in the art. The active component may be purified from the herb itself in any form (e.g., fruit, seed, spore, flower, leaves, stalk, root, rhizomes, etc.), the culture media of the organism, the decoction of a mixture of the present herbal combination, etc. Various techniques that may be employed in the purification include filtration, selective precipitation, extraction with organic solvents, extraction with aqueous solvents, column chromatography, high performance liquid chromatography (HPLC), etc. (Zubrick, The Organic Chem Lab Survival Manual Third Edition New York: John Wiley & Sons, Inc., 1992; Scopes Protein Purification Principles and Practice (2nd ed.), New York: Springer-Verlag, 1987; each of which is incorporated herein by reference). As would be appreciated by one of skill in the art, the active components may be proteins, peptides, nucleic acids, natural products, terpenes, alkaloids, proteoglycans, polysaccharides, lipids, triglycerides, etc., or combinations thereof, and therefore, the purification procedure would depend on the nature of the component being purified.

According to certain embodiments, the herbal extracts are those using an isolated fraction from one or more herbs of the present invention. An isolated fraction means in this sense a subsidiary amount of herbal substances which has been removed, for example, by chromatographic means, distillation, precipitation, extraction, filtration or in other ways from the herb itself. In other embodiments, the herbal extracts and fractions are removed therefrom by chromatography, distillation, precipitation, or extraction. Such extraction and isolation techniques are well known to one of ordinary skill in the art. The details of some of these techniques are set forth in the Examples section below.

In certain embodiments of the present invention, the herbal extracts, or active components thereof, are utilized in the form of lyophilates, concentrates, solutions or suspensions.

According to other embodiments of the present invention, the presence and purity of the active compound is assessed by chemical methods including nuclear magnetic spectroscopy (NMR), mass spectroscopy, infrared spectroscopy (IR), ultraviolet visible spectroscopy, elemental analysis, polarimetry, refractometry, etc. Such methods of analysis are known to one of ordinary skill in the art.

Although certain exemplary embodiments are described above and herein, it will be appreciated that the herbal formulas of the invention can be prepared according to the methods described generally above using appropriate starting materials by methods generally available to one of ordinary skill in the art.

Pharmaceutically Acceptable Compositions

1. Active Components

As discussed above, the present invention provides an herbal formula that is useful for the treatment of food allergy. Accordingly, in another aspect of the present invention, pharmaceutically acceptable compositions are provided, wherein these compositions comprise the herbal formula as described herein, and further comprise a pharmaceutically acceptable carrier, adjuvant, or vehicle. In certain embodiments, these compositions optionally further comprise one or more additional therapeutic agents.

Other embodiments contemplated by the present invention include those where any active component, or combination thereof, is provided in said pharmaceutically acceptable composition. Such active components, and combinations thereof, may be provided by any methods known to one of ordinary skill in the art and by the methods described herein.

Further embodiments contemplated by the present invention include those where extracts, or lyophilates thereof, are provided in said pharmaceutically acceptable composition.

In certain embodiments, the present herbal formulas, extracts thereof, and pharmaceutically acceptable compositions thereof are administered orally. However, other routes of administration may also be utilized. For example, in some embodiments of the invention, pharmaceutical compositions may be delivered to mucous membranes, for example, by inhalation or injection. In general, the pharmaceutically acceptable compositions of the present invention can be administered to humans and/or to other animals, orally, rectally, parenterally, intracisternally, intravaginally, intraperitoneally, topically (as by powders, ointments, or drops), bucally, or as an oral or nasal spray.

2. Adjuvants

A variety of compounds are known in the art to have specific or general immunostimulatory effects. Such compositions are commonly referred to as "adjuvants". A large number of adjuvant compounds is known; a useful compendium of many such compounds is prepared by the National Institutes of Health and can be found on the world wide web at the following address: niavd.nih.gov/daids/vaccine/pdt/compendium/pdf, incorporated herein by reference; see also Allison Dev. Biol. Stand. 92:3-11, 1998; Unkeless et al. Annu Rev. Immunol. 6:251-281, 1998; Phillips et al. Vaccine 10:151-158, 1992; each of which is incorporated herein by reference). Adjuvants are characterized by an ability to stimulate Th1 responses preferentially over Th2 responses and/or to down-regulate Th2 responses. In fact, in certain embodiments of the invention, adjuvants that are known to stimulate Th2 responses are avoided. Particularly adjuvants include, for example, preparations (including heat-killed samples, extracts, partially purified isolates, or any other preparation of a microorganism or microorganism component sufficient to display adjuvant activity) of microorganisms such as *Listeria monocytogenes* or others (e.g., Bacille Calmette-Guerin [BCG], *Corynebacterium* species, *Mycobacterium* species, *Rhodococcus* species, *Eubacteria* species, *Bortadella* species, and *Nocardia* species), and preparations of nucleic acids that include unmethylated CpG motifs (see, for example, U.S. Pat. No. 5,830,877; and published PCT applications WO 96/02555, WO 98/18810, WO 98/16247, and WO 98/40100, each of which is incorporated herein by reference). Other adjuvants reported to induce Th1-type responses and not Th2-type responses include, for example, Aviridine (N,N-dioctadecyl-N'N'-bis (2-hydroxyethyl) propanediamine) and CRL 1005.

In some embodiments of the invention, the adjuvant is associated (covalently or non-covalently, directly or indirectly) with the herbal formulation so that adjuvant and formulation can be delivered substantially simultaneously to an individual, optionally in the context of a single composition. In other embodiments, the adjuvant is provided separately. Separate adjuvant may be administered prior to, simultaneously with, or subsequent to herbal formulation administration. Where adjuvant and formulation are provided together, any association sufficient to achieve the desired immunomodulatory effects may be employed.

3. Carriers

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

4. Dosage Forms and Formulations

Liquid dosage formulations include, but are not limited to, pharmaceutically acceptable emulsions, microemulsions, solutions, suspensions, syrups and elixirs. In addition to the herbal formula, or active component(s) derived therefrom, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the liquid dosage forms can also include, for example, wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms may be made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are include suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms (e.g. for oral administration) include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The herbal formula, or active components derived therefrom, of the present invention can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of the herbal formula, or active components derived therefrom, of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of the herbal formulation to the body. Such dosage forms can be made by dissolving or dispensing the compound in the proper medium. Absorption enhancers can also be used to increase the flux of the herbal formulation across the skin. The rate can be controlled by either providing a rate controlling membrane or by dispersing the compound in a polymer matrix or gel.

In certain embodiments, the herbal formula, or active components derived therefrom, of the present invention, or composition thereof, may be administered as a lyophilate, an aqueous solution, an alcoholic solution, or a syrup. One of ordinary skill in the art would recognize that the preparation of the present herbal formula as; a lyophilate is accomplished directly by lyophilizing an aqueous extract of said herbal formula or, alternatively, a partially aqueous extract. By "partially aqueous" is meant that the herbal extract is obtained by a solution that contains water but is not entirely water. Such partially aqueous solutions that are amenable to lyophilization are known in the art. According to an alternate embodiment, the herbal extract is obtained in alcohol, such as ethanol, or other suitable solvent and that solvent is removed and replaced thereby with water. The resulting aqueous solution is then subjected to lyophilization to obtain the lyophilate of the herbal formula for administration.

In other embodiments, the herbal formula of the present invention is formulated into a syrup for pediatric use. Such syrups may include additional flavors and/or colorants to aid in the administration to children. Additionally, the present invention contemplates the preparation of an herbal tea. Such a tea can be prepared by dissolving or steeping the herbs of the present invention in the proper medium, such as hot water.

Uses of the Herbal Formulation and Pharmaceutically Acceptable Compositions Thereof In yet another aspect of the present invention, a method for treating or lessening the severity of food allergy is provided, wherein said method comprises administering an effective amount of an herbal formula, or a pharmaceutically acceptable composition thereof, to a patient in need thereof. In certain embodiments of the present invention, an "effective amount" of the herbal formula or pharmaceutically acceptable composition thereof is that amount effective for alleviating or attenuating one or more symptoms associated with food allergy.

In certain embodiments, the present invention relates to a method for treating or lessening the severity of peanut allergy is provided, wherein said method comprises administering an effective amount of the present herbal formula, or a pharmaceutically acceptable composition thereof, to a patient in need thereof.

According to yet another embodiment, the present invention provides a method of treating, lessening the severity of, or preventing anaphylactic shock, wherein said method comprises administering to a patient in need thereof; an herbal formula of the present invention or a pharmaceutically acceptable composition thereof.

Another aspect of the present invention relates to a method of preventing allergy, or preventing or lessening the severity of one or more allergy-related symptoms, wherein said method comprises administering to a patient in need thereof, an herbal formula of the present invention or a pharmaceutically acceptable composition thereof.

In certain embodiments, the herbal formula prevents, or lessens the severity of, allergy or one or more allergy-related symptoms for 6-12 months after administration of an herbal formula of the present invention or a pharmaceutically acceptable composition thereof. In other embodiments, said herbal formula prevents, or lessens the severity of, allergy or one or more allergy-related symptoms for 3-6 months. In yet other embodiments, said herbal formula prevents, or lessens the severity of, allergy or one or more allergy-related symptoms for 1-3 months.

The herbal formula and compositions thereof, according to the method of the present invention, may be administered using any amount and any route of administration effective for treating or lessening the severity of food allergy. The exact amount required will vary from subject to subject, depending on the species, age, and general condition of the subject, the severity of the infection, the particular agent, its mode of administration, and the like. The herbal formula of the invention may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The pharmaceutically acceptable compositions of this invention can be administered to humans and animals orally, rectally, parenterally, intracisternally, intravaginally, intraperitoneally, topically (as by powders, ointments, or drops), bucally, as an oral or nasal spray, or inhaled. In certain embodiments, the herbal formula of the invention may be administered orally or parenterally at dosage levels of about 0.01 mg/kg to about 50 mg/kg and, alternatively, from about 1 mg/kg to about 25 mg/kg, of subject body weight per day, one or more times a day, to obtain the desired therapeutic effect.

In certain embodiments, the pharmaceutically acceptable compositions of the present invention are administered orally.

The present invention relates to an herbal formula for the treatment of food allergy, and compositions comprising said formula, wherein said formula consists of Ling-Zhi, Wu Mei, Chuan Jiao, Huang Lian (Chuan), Huang Bai, Gan Jiang, Gui Zhi, Ren Shen (Hong), and Dang Gui (Shen). In particular, the present invention provides methods of treating or lessening the severity of food allergy and/or food allergy-related symptoms in a patient in need thereof comprising the step of administering to said patient an herbal formula of the present invention.

The present invention also relates to a method of treating peanut allergy, in a patient in need thereof, wherein said method comprises administering to said patient an herbal formula consisting of Ling-Zhi, Wu Mei, Chuan Jiao, Huang Lian (Chuan), Huang Bai, Gan Jiang, Gui Zhi, Ren Shen (Hong), and Dang Gui (Shen), or a pharmaceutically acceptable composition thereof.

Another embodiment of the present invention relates to methods, as described herein, in which one or more chemical substances, in particular active substances, isolated from the herbs are used. By these are meant in particular also single substances isolated from one or more of Ling-Zhi, Wu Mei, Chuan Jiao, Huang Lian (Chuan), Huang Bai, Gan Jiang, Gui Zhi, Ren Shen (Hong), and Dang Gui (Shen) extracts, so-called natural substance isolates, as are also mown, for example, to one or ordinary skill in the art. The use of these isolated active substances has the advantage that it is generally necessary to use considerably smaller amounts of substance and, moreover, more specific effects are often achieved than with whole extracts or tablets.

Without wishing to be bound by any particular theory, the herbal formulas and compositions thereof are particularly useful for treating or lessening the severity of a disease, condition, or disorder where Th2 response is implicated in the disease, condition, or disorder. Accordingly, another embodiment relates to a method of down regulating the activation of Th2 in a patient in need thereof, wherein said method comprises administering to said patient an herbal formula of the present invention or pharmaceutically acceptable composition thereof.

The present herbal formulas and pharmaceutically acceptable compositions thereof may be employed to treat existing allergic symptoms (i.e., to reduce the severity, intensity, and/or duration of such symptoms). In such cases, the formulas or compositions thereof are administered to an individual after allergic symptoms have developed.

Alternatively or additionally, the composition may be used to prevent or delay the onset of symptoms in an individual who has previously suffered from allergic symptoms, or to reduce the severity, intensity, or duration of subsequently-developed symptoms. In certain embodiments, one or more antigens have been identified that is known to have induced, or at least to be correlated with, the onset of such prior allergic attacks. In such cases, the present formulas, and pharmaceutically acceptable compositions thereof are administered either prior to the onset of symptoms after a subsequent encounter with the antigen, or prior to the encounter.

The present formulas and compositions thereof may also be administered prior to the development of allergic sensitivity to a particular antigen. In certain embodiments, the compositions are administered substantially concurrently with exposure to an antigen that has not previously been associated with an allergic reaction in the individual. Without wishing to be bound by any particular theory, we propose that the present formulas and pharmaceutically acceptable compositions thereof may encourage the individual to adopt a Th1 response to the antigen. Given the mutually inhibitory aspects of Th1 and Th2 responses, the initial development of a Th1 response may inhibit, delay, or prevent subsequent Th1 reactions that could otherwise result in food allergy and related symptoms.

In other embodiments of the present invention, said formula is administered in combination with one or more additional therapeutic agents. For example, the herbal formulas of the present invention may be administered in combination with anti-histamines (e.g., inhaled, injected, or orally delivered anti-histamines), decongestants, etc. used to treat food allergy symptoms.

In some cases, in will be desirable to provide the present herbal formulations in combination with one or more cytokines or inducing agents, to promote and/or reflect a reduction in Th2 responses and/or an increase in Th1 responses to the relevant antigen. In certain embodiments of the invention, herbal formulations are provided in combination with one or more Th1 stimulating cytokines (e.g., IL-12, IL-2, IL-18, IL-1β or fragments thereof, IFNα, and/or IFNγ, etc.) and/or one or more Th1 inducing agents (e.g., factors such as LPS, CD40, CD40 ligand, BCGs, oligonucleotides containing CpG motifs, TNFα, and microbial extracts such as preparations of Staphylococcus aureus, heat killed Listeria, etc.). Alternatively or additionally, the herbal formulations may be provided in combination with one or more Th1 cytokines (e.g., IL-1β, IL-2, IL-12, IL-18, IFNα, IFNγ, TNFβ, etc.). In certain embodiments, said cytokines are administered within the pharmaceutically acceptable composition of the present invention, thus forming a single dosage form. In other embodiments, said cytokines are administered contemporaneously with the pharmaceutically acceptable composition of the present invention as a separate dosage form.

It will also be appreciated that the herbal formulas and pharmaceutically acceptable compositions of the present invention can be employed in combination therapies, that is, the herbal formulas of the present invention and pharmaceutically acceptable compositions thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the herbal formula of the present invention may be administered concurrently with another agent used to treat the same disorder), or they may achieve different effects (e.g., control of any adverse effects). As used herein, additional therapeutic agents that are normally administered to treat, lessen the severity of, or prevent a particular disease, or condition, are known as "appropriate for the disease, or condition, being treated."

The herbal formulas of the present invention may be administered to a subject in combination with one or more other therapeutic treatments. For example, anti-histamine administration is an established and accepted treatment for food allergy. Thus, the herbal formulations of the present invention may desirably be administered in combination with standard or reduced anti-histamine treatments, whether inhaled or systemic. The herbal formulations of the present invention may also be administered in combination with additional therapeutic immunotherapy or rush immunotherapy. Immunotherapies are typically administered in order to induce tolerance in a sensitized individual (for a more detailed description of immunotherapy, please see U.S. Provisional Patent Application, U.S. Ser. No. 60/213,765, filed Jun. 23, 2000; incorporated herein by reference).

Other therapeutic agents, known for the treatment of food allergy, may be administered with the herbal formulas, or pharmaceutically acceptable compositions thereof, of the present invention. Such agents also include, but are not limited to, antihistamines such as diphenhydramine (Benadryl®) or chlorpheniramine maleate (Chlor-Trimeton®), epinephrine (Primatene Mist®), bronchodilators, either inhaled or systemic including albuterol (Proventil® or Ventolin®), corticosteroids, administered intra venously, orally or topically, and combination therapy such as Advair®, to name a few. It will be appreciated that these therapeutic agents may be administered with the present herbal formulas, and pharmaceutically acceptable compositions thereof, in a single dosage form or separately.

The present herbal formulas may be administered, whether alone or in combination with one or more other agents or compounds, in the context of an encapsulated system. A variety of encapsulation systems are known in the art (see, for example, discussions in U.S. Ser. No. 60/169,330, filed Dec. 6, 1999, and incorporated herein by reference); any such system may be employed in accordance with the present invention. In certain embodiments of the invention, the encapsulation material itself may offer adjuvant activity. Also, encapsulation systems may desirably be associated with one or more targeting agents that facilitate delivery of the present compositions to relevant sites (e.g., mucosal membranes).

The amount of additional therapeutic agent present in the compositions of this invention will typically be no more than the amount that would normally be administered in a composition comprising that therapeutic agent as the only active agent. In certain embodiments, the amount of additional therapeutic agent in the presently disclosed compositions will range from about 50% to 100% of the amount normally present in a composition comprising that agent as the only therapeutically active agent.

These and other aspects of the present invention will be further appreciated upon consideration of the following Examples, which are intended to illustrate certain particular embodiments of the invention but are not intended to limit its scope, as defined by the claims.

EXAMPLES

The effects of herbal formulas of the present invention and pharmaceutically acceptable compositions thereof may be studied in humans or in any available in vivo or in vitro model system. Animal models are particularly useful for the identification, characterization, and analysis of a particular composition's effects. Ideally, a model system should reflect closely at least some aspect of the disease pathology in man (or in another organism to which composition of the present invention is to be administered for the treatment of allergy), should be reliable and reproducible, should allow objective measurements of one or more physiologically-relevant parameters, should respond to one or more known therapeutic agents in a manner similar to that observed in man (or the suffering organism), and/or should offer a large number of reagents with which the immune system can be analyzed.

A variety of animal models, including those in guinea pigs, rabbits, sheep, dogs, monkeys, and mice have been developed that can usefully be employed to characterize the herbal formulas of the present invention and pharmaceutically acceptable compositions thereof (see, for example, Kay (ed.) Allergy and Allergic Diseases Blackwell Science, Ltd., Oxford. pp. 1037-1110, 1997; McCaslcill et al. "Anaphylaxis Following Intranasal Challenge of Mice Sensitized with Ovalbumin" *Immunology* 51:669-677, 1984; U.S. patent application Ser. No. 09/518,246, filed Mar. 3, 2000; each of which is incorporated herein by reference).

Those of ordinary skill in the art will recognize that the particular mouse strain or route of administration of sensitizing antigen may not be critical in developing a mouse model system for use in characterizing the herbal formulas of the present invention. For example, Renz et al. have described a BALB/c mouse sensitized with aerosolized ovalbumin over a 10-day period (Renz et al., J. Exp. Med. 177:1175, 1993; incorporated herein by reference). These mice show elevated levels of ovalbumin-specific IgE and infiltration of eosinophils into the airway following bronchial challenge. Wills-Karp et al. have described an asthmatic A/J mouse model sensitized by intraperitoneal administration of antigen, followed by intratracheal challenge (Gavett et al., *Am. J. Respir. Cell Mol. Biol.* 10:587, 1994; Keane-Myers et al., *J. Immunol.* 161:919, 1998; Wills-Karp et al., *Science* 282:2258, 1998; Grunig et al., *Science* 282:2261, 1998; each of which is incorporated herein by reference). In certain embodiments, the sensitizing antigen is administered to the animal via the same route the animal would encounter the allergen in nature (e.g., oral for food allergens, IV or parenteral for venoms, inhaled for pollens or dust allergens, intradermal for latex). In another embodiment, the mouse is sensitized to the allergen using alum as an adjuvant.

Example 1

PN sensitization/challenge and herbal formula treatment: Mice (5 week old female C3H/HeJ) were sensitized and challenged with PN by methods substantially similar to those known in the art. Mice were sensitized intragastrically (ig) with PN (10 mg/mouse) plus cholera toxin (20 µg/mouse) weekly for 3 weeks and boosted at weeks 5 and 7. At week 3 PN sensitized mice were treated ig with equal doses of FAHF-1 and FAHF-2 (21 mg/mouse in 0.5 ml water) respectively twice daily for 7 weeks (This dose was determined based on a conversion table of equivalent effective dose ratios from humans to animals based on body surface area. Water (sham) treatment and naïve mice served as controls. One week after the last treatment, all mice were challenged with PN. See FIG. 1.

Example 2

Figure 2:
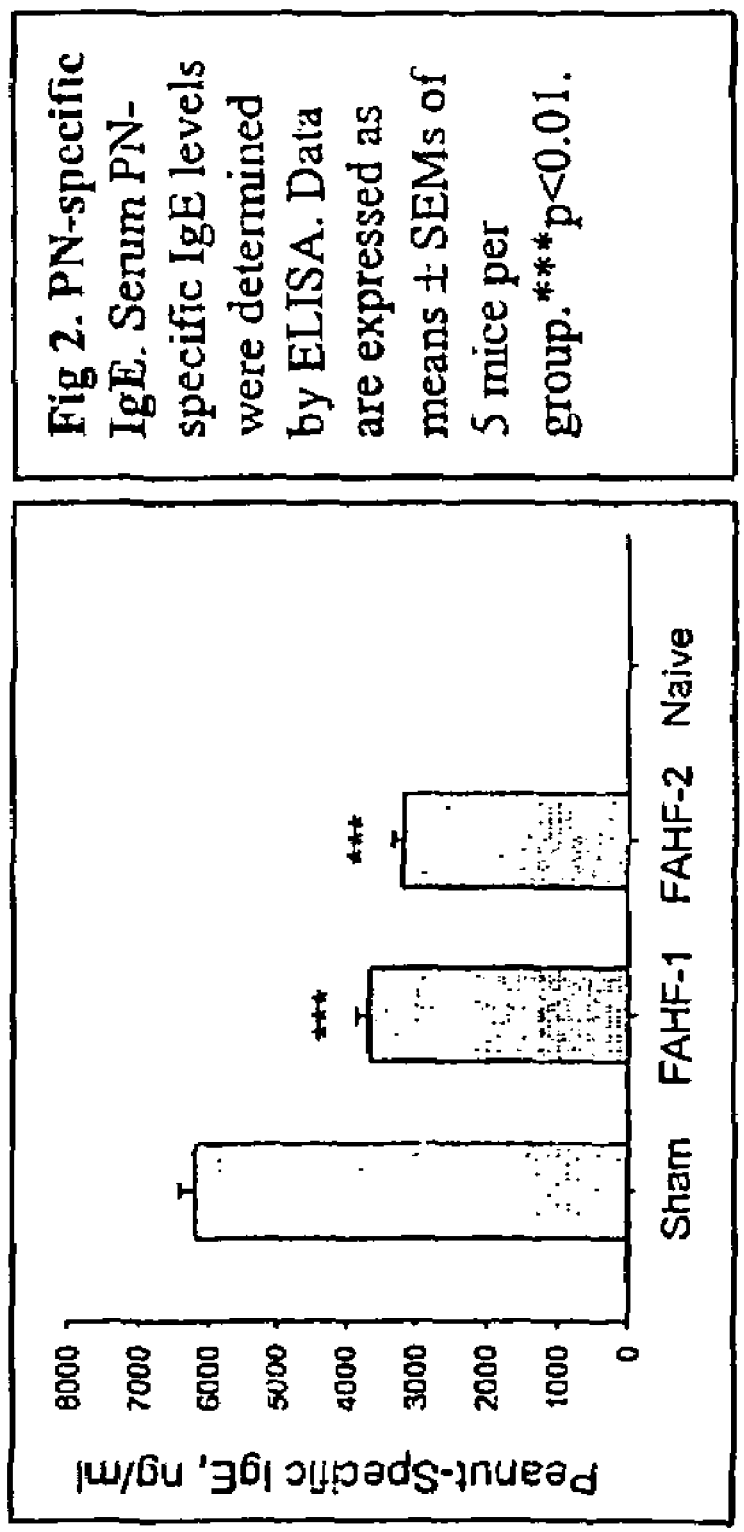
FIG. 2 depicts the PN-specific IgE levels.

Effect of FAHF-2 on PN-specific IgE: PN induced anaphylaxis is an IgE mediated type I hypersensitivity. To determine the effect of FAHF-2 on PN-specific IgE production, we monitored IgE levels following treatment. The IgE levels at the time challenge are shown in FIG. 2. IgE levels were significantly reduced in both FAHF-1 and FAHF-2 treated groups as compared with sham treated group (p<0.01); no difference was observed between these two treatments.

Example 3

Figure 3:
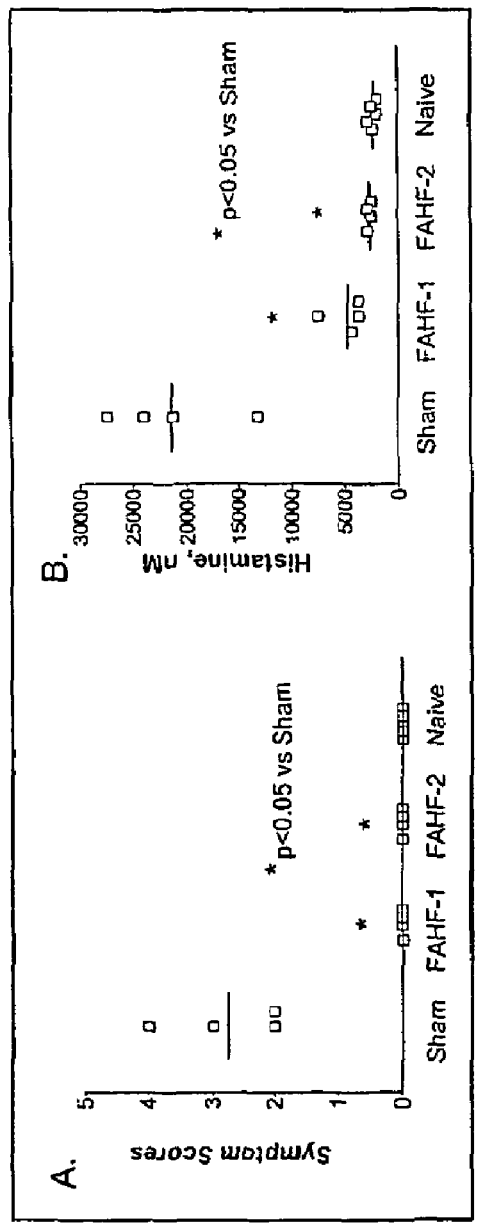
FIG. 3A shows the anaphylactic symptom scores of dosed mice as compared with naïve and sham mice and FIG. 3B shows the plasma histamine levels of dosed mice as compared with naïve and sham mice.
Figure 4:
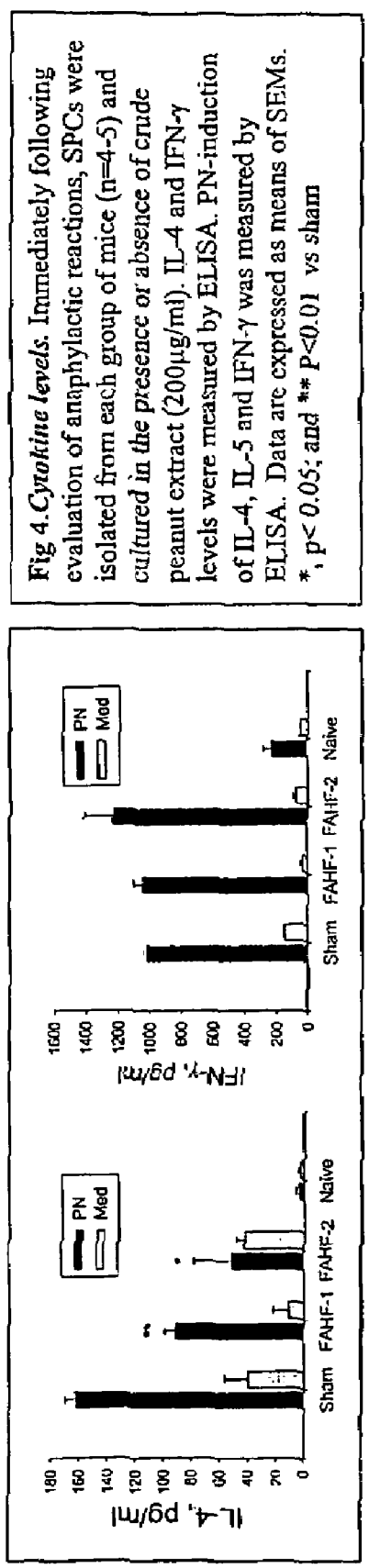
FIG. 4 depicts the cytokine levels following anaphylactic reactions.

Effect of FAHF-2 on Anaphylactic Reactions and Plasma Histamine Levels: Anaphylactic symptom scores were evaluated 30 minutes following the last PN challenge, wherein the following scoring system was utilized. Specifically, the scores are as follows: 0—no symptoms; 1—scratching and rubbing around the nose and head; 2—puffiness around eyes & snout; pilar erecti, diarrhea, reduced activity or standing still with an increasing respiratory rate; 3—wheezing, labored respiration, cyanosis around the mouth and the tail; 4—no activity after prodding, or tremor and convulsion; 5—death. We found that 100% of mice in the sham treated group developed anaphylactic reactions. See FIG. 3A. Consistent with our previous finding, no mouse in the FAHF-1 treated group exhibited any sign of anaphylaxis. FAHF-2 also completely blocked anaphylactic reactions. Histamine is one of the major mediators associated with anaphylactic symptoms. Plasma histamine levels in the FAHF-2 treated groups were significantly lower than the sham treated group and not different from naïve mice See FIG. 3B.

Example 4

Suppression of Th2 Cytokines by FAHF-2: We previously found that FAHF-1 suppressed Th2 cytokine production by splenocytes (SPCs) of PN allergic mice. In this assay, we also found that IL-4 and IL-5 production by SPCs from FAHF-2 as well as FAHF-1 treated PN allergic mice were significantly reduced compared to sham treated mice. No difference in IFN-γ levels between treated and sham treated groups was observed.

Example 5

Comparing the Safety of FAHF-2 to FAHF-1: To determine possible toxicity we also tested both formulas for lethality (LD50 test): No mouse died after feeding 12 times the effective mouse daily dose of FAHF-1 or FAHF-2 within 12 hours. We monitored these mice for an additional week and none died (data not shown). In a second set of experiment, we fed the mice 24 times the effective mouse daily dose of FAHF-1 or FAHF-2 where the sham group was fed only water. No mouse died in either group within 12 hours. We monitored these mice for an additional 2 weeks. All mice appeared healthy (Table 2). We were unable to generate an LD 50 because the maximum possible doses produced no mortality. To further assess safety, organ specimens from mice tested above were subjected to biochemical analysis of liver and kidney functions two weeks after feeding. No abnormality in kidney and liver functions was detected (Table 2). In addition, no abnormal WBC, RBC, Hb, or PLT was observed by CBC testing. Taken together, these results demonstrated that the efficacy and safety of FAHF-2 are comparable to FAHF-1.

TABLE 2

Safety Assessment of FAHF-2 Compared with FAHF-1

| | Treatment | Death (12 h) | Death (2 wks) | Morbidity (%) | Mortality (%) | BUN | AST | CBC |
|---|---|---|---|---|---|---|---|---|
| Group 1 | FAHF-1 | 0/5 | 0/5 | 0 | 0 | Normal | Normal | Normal |
| Group 2 | FAHF-2 | 0/5 | 0/5 | 0 | 0 | Normal | Normal | Normal |
| Group 3 | Sham | 0/5 | 0/5 | 0 | 0 | Normal | Normal | Normal |

Example 6

Figure 5:
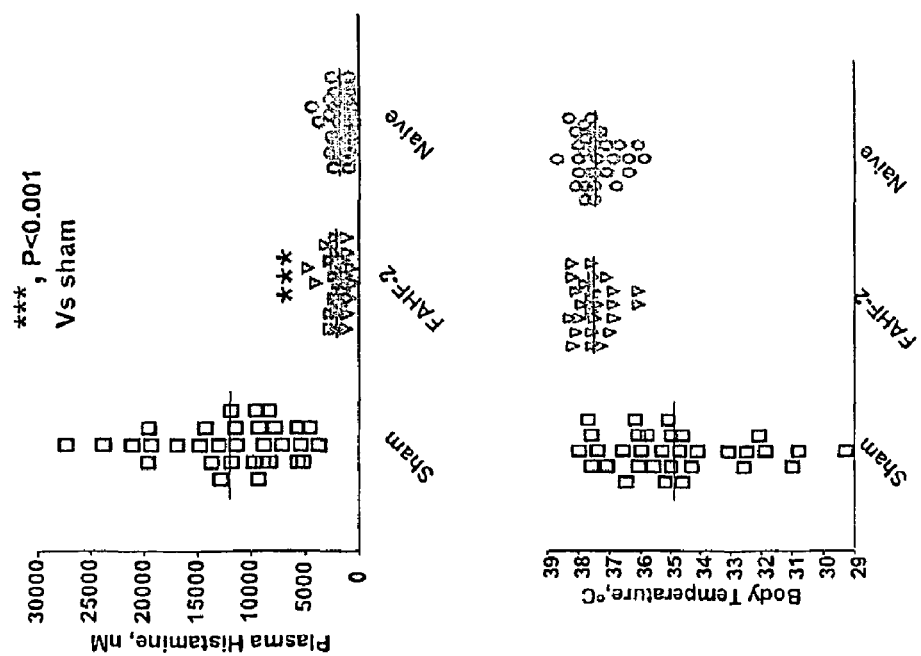
FIG. 5 shows the plasma histamine levels and the body temperature in FAHF-2 treated mice.
Figure 11:
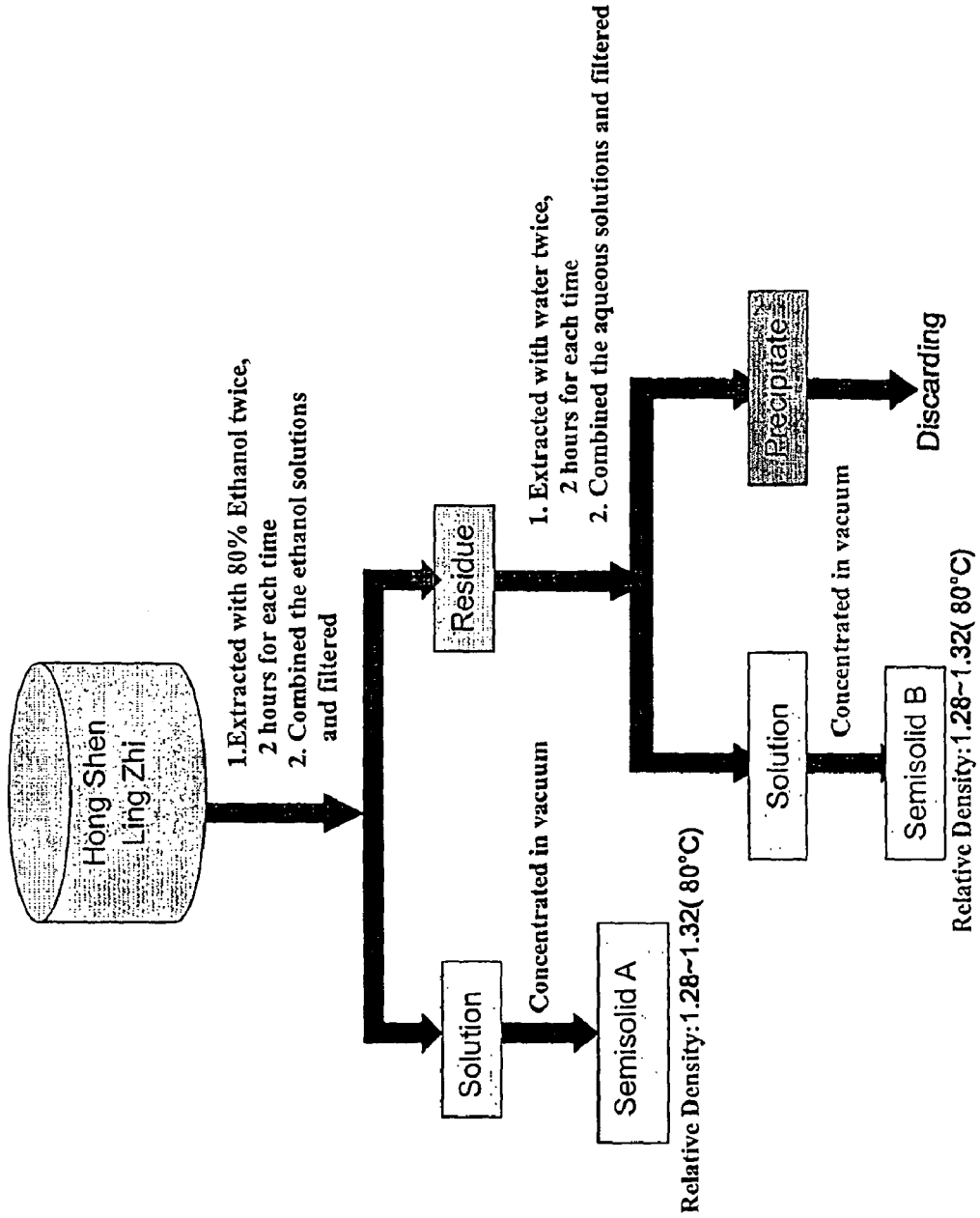
FIG. 11 shows the flow chart for the manufacture of FAHF.
Figure 12:
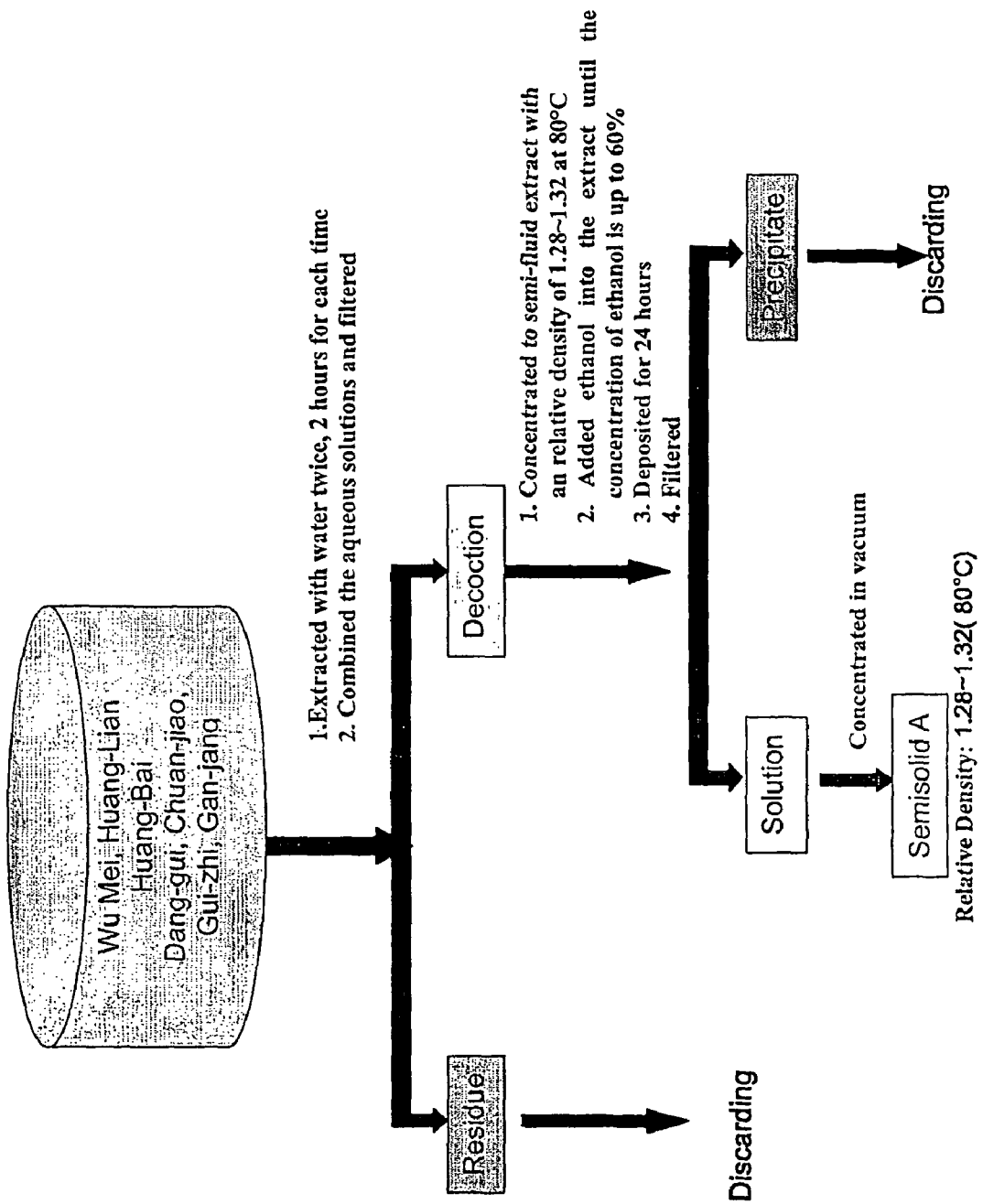
FIG. 12 shows the flow chart for the manufacture of FAHF.
Figure 13:
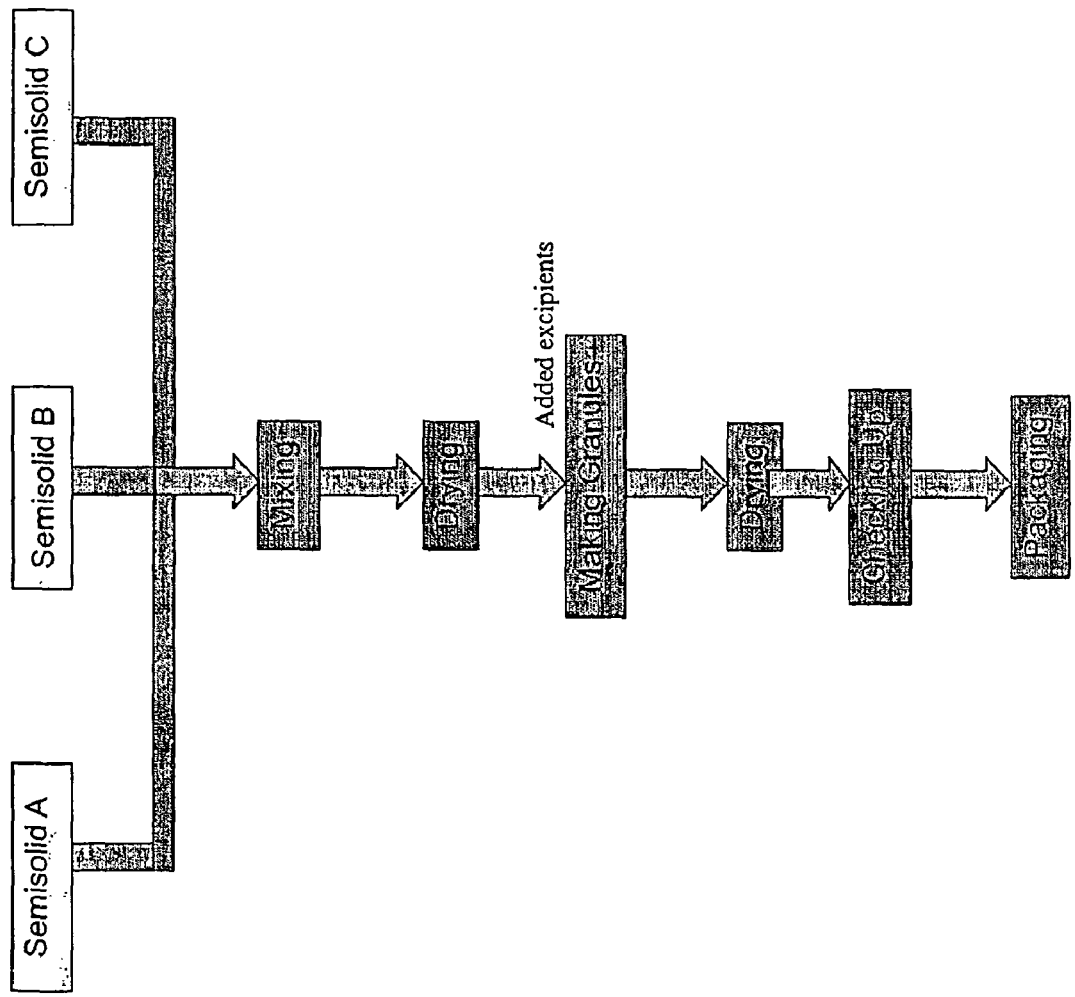
FIG. 13 shows the flow chart for the manufacture of FAHF.

Consistent Effect of Manufactured FAHF-2 on Peanut Allergy: Having determined the efficacy and safety of FHAF-2 manufacturing methods were established to produce FAHF-2 in collaboration with Beijing Shen Hua Shi Di Medical Technology, Beijing China to obtain manufactured herbal product made by a modern factory using classical herbology and Good Manufacturing Practices (GMP) standards. This manufacturing process for preparing FAHF-2 is described in FIGS. 11, 12, and 13. Table 3 shows manufactured FAHF-2 completely blocked the anaphylactic symptoms following peanut challenged at 1 week (experiment 1 and 2), 3 weeks (experiment 3) and 5 weeks (Experiment 4 and 5) after discontinuing the treatment. Consistently, plasma histamine levels and the body temperature in FAHF-2 treated mice in all experiments were normal following peanut challenge. See FIG. 5.

TABLE 3

Anaphylaxis to PN challenge

| | Sham | | FAHF-2 | | Naïve | |
|---|---|---|---|---|---|---|
| Experiment | n/total | % | n/total | % | n/total | % |
| 1 * | 4/4 | 100 | 0/4 | 0 | 0/5 | 0 |
| 2 ** | 5/5 | 100 | 0/4 | 0 | 0/5 | 0 |
| 3 ** | 6/8 | 75 | 0/4 | 0 | 0/5 | 0 |
| 4 ** | 7/8 | 88 | 0/4 | 0 | 0/5 | 0 |
| 5 ** | 5/5 | 100 | 0/5 | 0 | 0/5 | 0 |
| Total | 27/30 | 90 | 0/21 | 0 | 0/25 | 0 |

* laboratory prepared product
** manufactured product

Example 7

Figure 6:
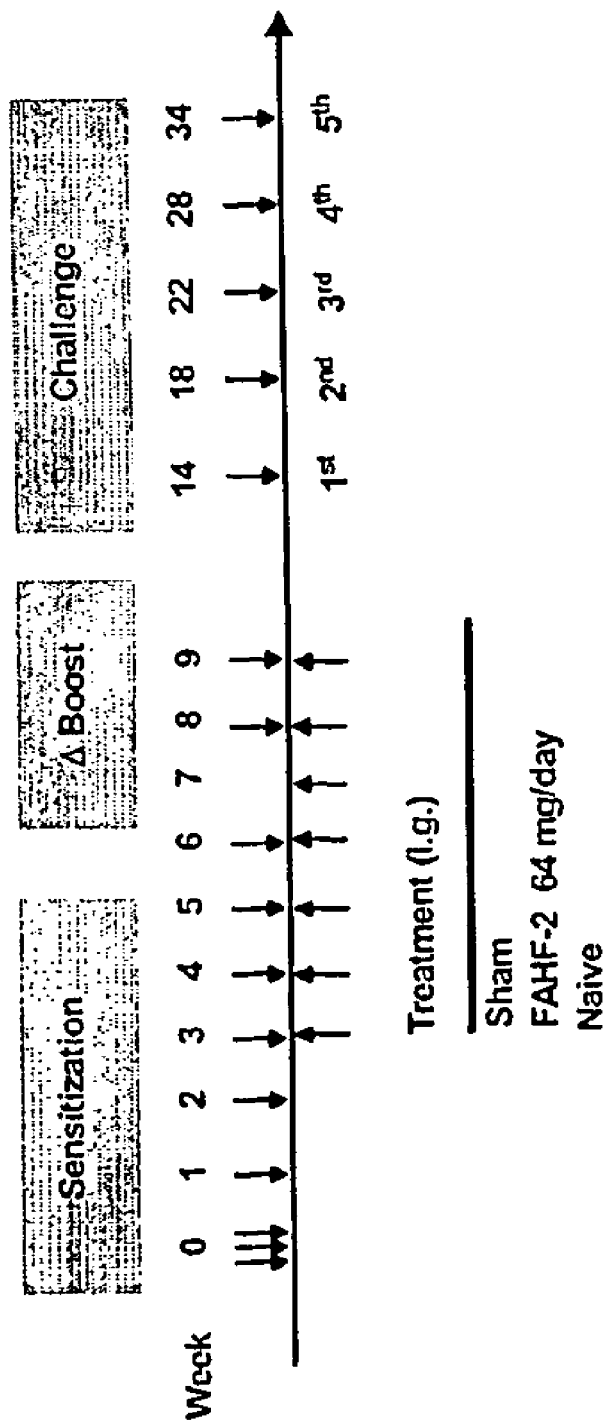
FIG. 6 depicts the dosing protocol for FAHF-2 prevented anaphylaxis.
Figure 7A:
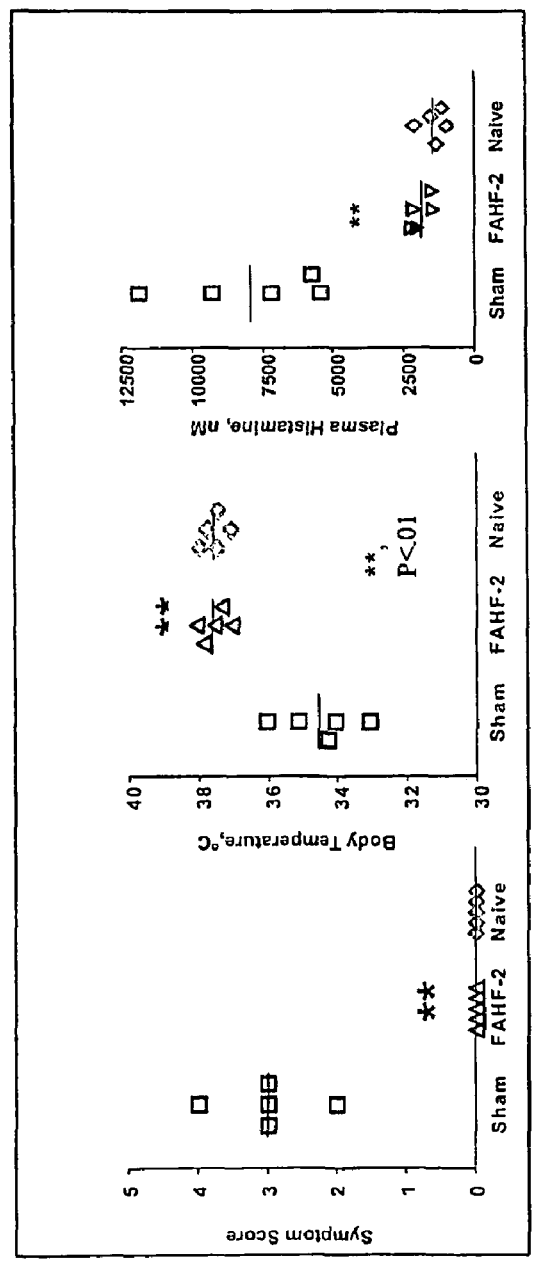
FIG. 7A shows the effect on anaphylactic reactions and plasma histamine at week 14.
Figure 7B:
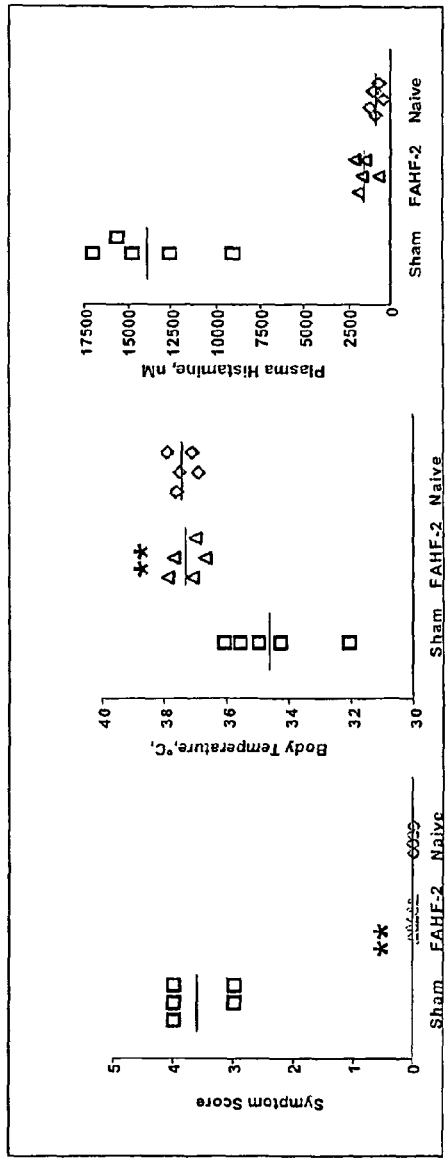
FIG. 7B shows the effect on anaphylactic reactions and plasma histamine at week 18.
Figure 7C:
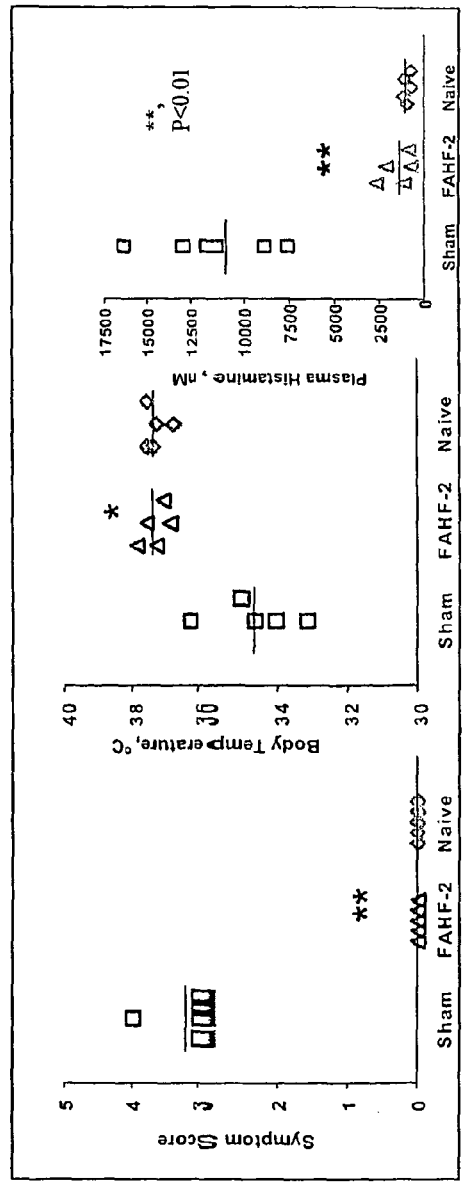
FIG. 7C shows the effect on anaphylactic reactions and plasma histamine at week 22.
Figure 7D:
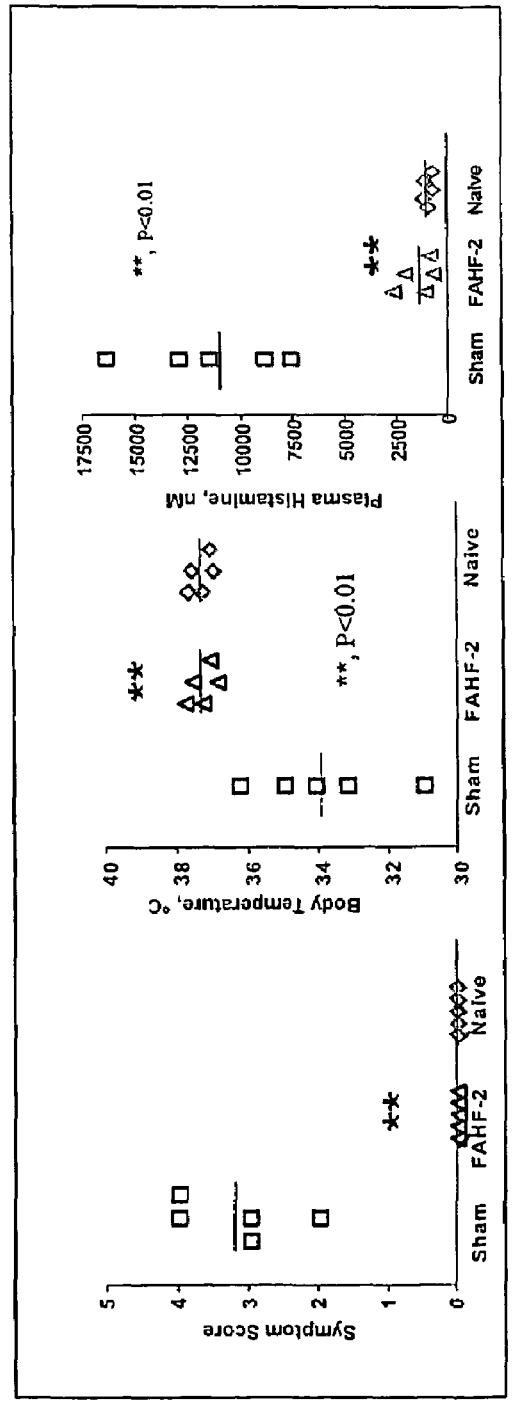
FIG. 7D shows the effect on anaphylactic reactions and plasma histamine at week 28.
Figure 7E:
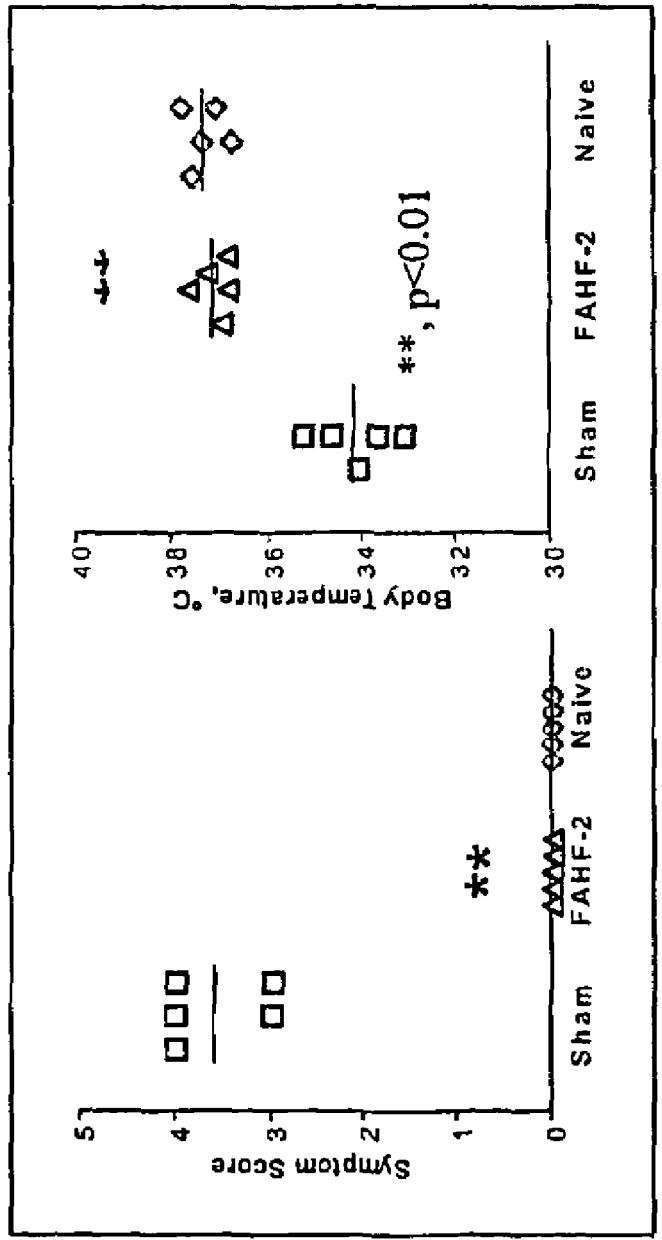
FIG. 7E shows the effect on anaphylactic reactions and plasma histamine at week 34.
Figure 8:
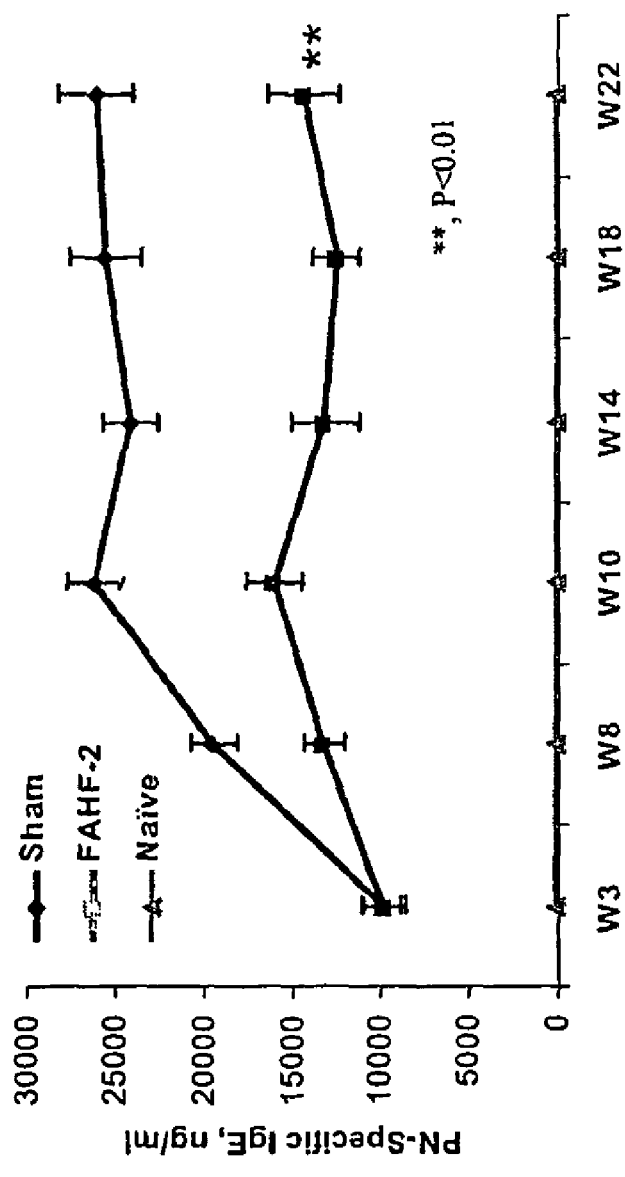
FIG. 8 depicts the effects on peanut-specific IgE.

Long Lasting Effect of FAHF-2 on Peanut Allergy: With conventional drug therapy, such as corticosteroid treatment of allergic diseases, allergy symptoms frequently re occur shortly after discontinuing treatment. It is traditionally believed that Chinese herbal medicine therapies have persistent effects on chronic diseases. Form the results obtained above, we found that FAHF-2 testament prevented anaphylaxis 5 weeks after the discontinuation of the treatment, suggesting that FAHF-2 may have a long lasting effect on peanut allergy. We recently determined how long the protective effect of FAHF-2 against peanut anaphylaxis to peanut re exposure persists. We treated peanut allergic mice with FAHF-2 beginning at week 3 following the initial peanut sensitization for 7 weeks and then discontinued the treatment. We then challenged the mice every 4-6 weeks. See FIG. 6. We found that the full protection against anaphylaxis by FAHF-2 lasted 6 months. See FIG. 7A through 7E. We also found that IgE levels were remained significantly lower in FAHF-2 treated group as compared with the sham treated group. See FIG. 8.

Example 8

Figure 9:
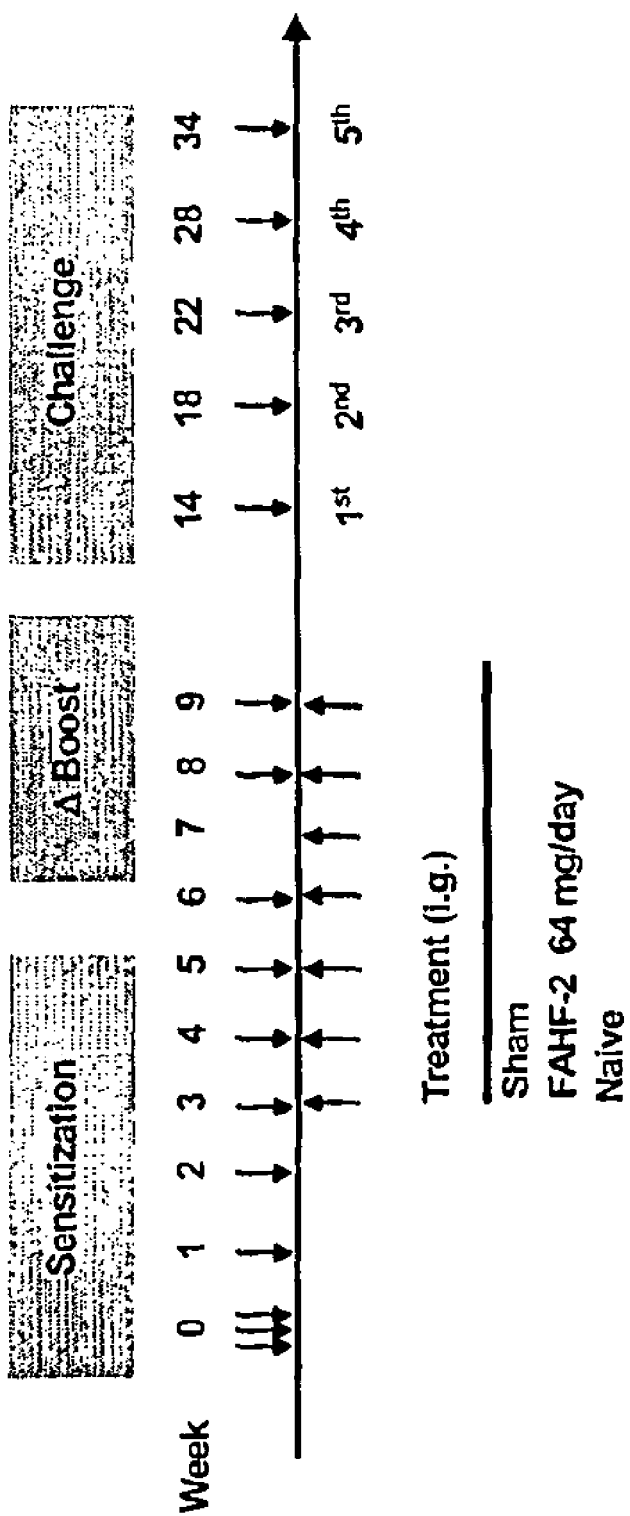
FIG. 9 depicts the dosing regimen used for the individual herbs.

Assessment of Individual Herb Components: Each of the individual herb components of FAHF-2 was subjected to the above assays. Specifically, each of the individual herbs were dosed according to FIG. 9 and the results of each assay are summarized below.

Effect of Individual Herbs on Anaphylaxis: Results were obtained by methods substantially similar to those described herein and are summarized in Table 4, below.

TABLE 4

Anaphylactic Reactions

| Treatment | Reactions At Challenge | % Anaphylaxis |
|---|---|---|
| Sham | 16/19 | 84% |
| Gan Jiang | 3/5 | 60% |
| Huang Liang | 3/5 | 60% |
| Gui Zhi | 6/7 | 86% |
| Chuan Jiao | 5/8 | 62% |
| Dang Gui | 5/5 | 100% |
| Huang Bai | 2/8 | 25% |
| Wu Mei | 6/7 | 86% |
| Ren Shen | 4/4 | 100% |
| Ling Zhi | 3/4 | 75% |
| FAHF-2 | 0/14 | 0% |
| Naive | 0/15 | 0% |

Reduction of Plasma histamine and modulation of IgE and IgG2a by individual herbs: Results were obtained by methods substantially similar to those described herein and are summarized in Table 5, below.

TABLE 5

Reduction of Plasma histamine and modulation of IgE and IgG2a

| Treatment | Reduction of Plasma Histamine (vs Sham) | PN-specific IgE (vs Sham) | PN-specific IgG2a (vs Sham) |
|---|---|---|---|
| Sham | | | |
| Can Jiang | ↓86% | ↓18% | ↓4.3% |
| Huang Liang | ↓89% | ↑13% | ↑15% |
| Gui Zhi | ↓53% | ↑552% | ↓51% |
| Chuan Jiao | ↓72% | ↑16% | ↓36% |
| Dang Gui | ↓25% | ↓6% | ↓16% |
| Huang bai | ↓79% | ↓13% | ↓9% |
| Wu Mei | ↓14% | ↓1% | ↓18% |
| Ren Shen | ↓4% | ↓10% | ↑19% |
| Ling Zhi | ↓6% | ↓50% | ↑4% |
| FAHF2 | ↓99% | ↓43% | = |
| Naive | ↓100% | NA | NA |

Figure 10:
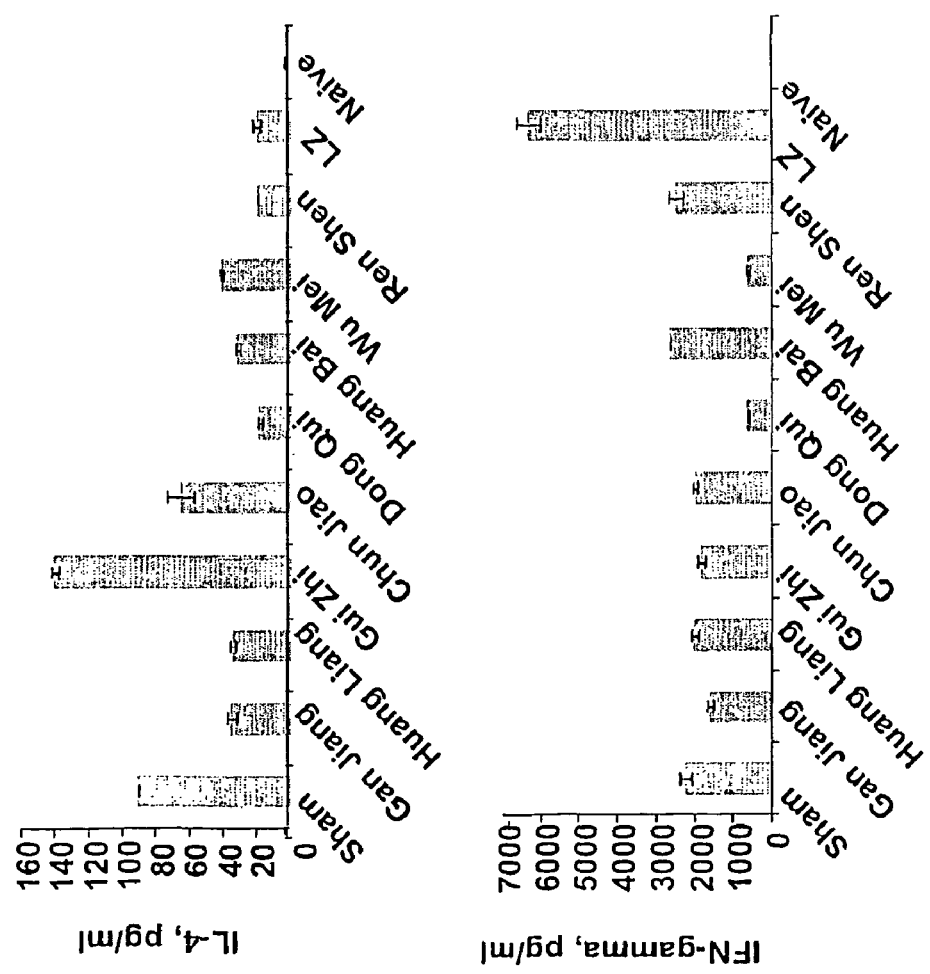
FIG. 10 depicts the resulting effects of each individual herb on cytokine production by spleenocytes.

Cytokine production by splenocytes: Results were obtained by methods substantially similar to those described herein and are summarized in FIG. 10.

Those of ordinary skill in the art will readily appreciate that the foregoing has provided descriptions of certain embodiments of the present invention; various modifications and alterations to these descriptions can be made without departing from the spirit or scope of the present invention, which is defined as set forth in the following claims.

We claim:

1. An herbal formula for treating or lessening the severity of food allergy, wherein said formula comprises an herbal mixture consisting of about 6-52% Ling-Zhi, about 11-58% Wu Mei, about 0.5-3% Chuan Jiao, about 3-16% Huang Lian, about 2.5-49% Huang Bai, about 2-15% Gan Jiang, about 1-9.5% Gui Zhi, about 3-16% Ren Shen, and about 3-16% Dang Gui, wherein the total percentage of Ling-Zhi, Wu Mei, Chuan Jiao, Huang Lian, Huang Bai, Gan Jiang, Gui Zhi, Ren Shen, and Dang Gui in the mixture is 100%.

2. A composition comprising the herbal formula according to claim 1 and a pharmaceutically acceptable carrier, adjuvant, or vehicle.

3. The composition according to claim 2, wherein said composition further comprises an additional therapeutic agent.

4. The composition according to claim 3, wherein said additional therapeutic agent is a corticosteroid.

5. The composition according to claim 3, wherein said additional therapeutic agent is an anti-histamine.

6. The composition according to claim 3, wherein said additional therapeutic agent is epinephrine.

7. The composition according to claim 3, wherein said additional therapeutic agent is a bronchodilator.

8. A method for treating or lessening the severity of food allergy, in a patient in need thereof, wherein said method comprises administering to said patient the herbal formula according to claim 1.

9. The method according to claim 8, wherein said food allergy is a peanut allergy.

10. A method of treating or lessening the severity of anaphylactic shock, in a patient in need thereof, wherein said method comprises administering to said patient the herbal formula according to claim 1.

* * * * *